(12) United States Patent
Winquist et al.

(10) Patent No.: US 6,841,053 B2
(45) Date of Patent: Jan. 11, 2005

(54) ELECTRONIC TONGUE AS OZONE DETECTOR

(75) Inventors: Fredrik Winquist, Linköping (SE);
Carina Högberg, Linköping (SE);
Christina Krantz-Rückler, Skärblacka (SE); Kjell Ekberg, Vaxholm (SE)

(73) Assignee: Otre AB, Stockholm (SE)

( * ) Notice: Subject to any disclaimer, the term of this patent is extended or adjusted under 35 U.S.C. 154(b) by 339 days.

(21) Appl. No.: 10/028,485

(22) Filed: Dec. 20, 2001

(65) Prior Publication Data

US 2002/0157946 A1 Oct. 31, 2002

Related U.S. Application Data

(60) Provisional application No. 60/270,046, filed on Feb. 20, 2001.

(30) Foreign Application Priority Data

Feb. 6, 2001 (SE) ............................................... 0100365

(51) Int. Cl.$^7$ .............................................. G01N 27/26
(52) U.S. Cl. ...................... 204/407; 204/406; 204/431; 205/785.5
(58) Field of Search ................................ 204/400, 406, 204/431, 407; 205/785.5

(56) References Cited

FOREIGN PATENT DOCUMENTS

| WO | WO 99/13325 | 3/1999 |
|---|---|---|
| WO | WO 99/46201 | 9/1999 |
| WO | WO 00/67011 | 11/2000 |

OTHER PUBLICATIONS

Smart et al, In Situ Voltammetric Membrane Ozone Electrode, Analytical Chemistry, 51, Dec. 1979, pp. 2315–2319.*

Ohmi, T. et al. "Ozone Decomposition in Ultrapure Water and Continuous Ozone Sterilization for a Semiconductor Ultrapure Water System". XP 000360633. Journal of the Electrochemical Society No. 11 (1992). pp. 3336–3345.

Sauter, D. et al. "Development of Modular Ozone Sensor System for Application in Practical Use". Sensors and Actuators B 69 (2000). pp. 1–9.

Winquist, F. et al. "Monitoring of Freshness of Milk by an Electronic Tongue on the Basis of Voltammetry". XP 000861720. Meas. Sci. Technol. 9 (1998). pp. 1937–1946.

International Search Report as completed on Feb. 20, 2002, by the ISA/EP in connection to International Patent Application No. PCT/SE01/02848.

P. Ivarsson et al., *Discrimination of Tea by Means of a Voltammetric Electronic Tongue and Different Applied Waveforms;* Sensors and Actuators B 76 (2001); pp. 449–455; PD; Jun. 1, 2001.

Holmin et al., *Compression of Electonic Tongue Data Based on Voltammetry–A Comparative Study;* Sensors and Actuators B 76 (2001); p. 455–464; PD; Jun. 1, 2001.

Winquist, Fredrik et al. "An Electronic Tongue Based on Voltammetry". Analytica Chimica Acta, vol. 357 (1997). pp. 21–31.

* cited by examiner

*Primary Examiner*—Kaj K. Olsen
(74) *Attorney, Agent, or Firm*—Jenkens & Gilchrist, P.C.

(57) ABSTRACT

An electronic tongue for the detection of ozone is based on voltammetry, and comprises at least one working electrode and a counter electrode, wherein the working electrode(s) is(are) made of one or more transition metals or Au, or alloys thereof, or alloys thereof with other metals. The data processing is made by multivariate analysis. The sensor can be implemented on-line or in-line in a processing plant where it is desirable to monitor and control ozone levels, e.g. sterilization and purification plants.

12 Claims, 16 Drawing Sheets

ELECTRONIC TONGUE AS OZONE DETECTOR

This application claims priority to Swedish Patent Application 0100365-6 filed on Feb. 6, 2001 and U.S. Provisional Application No. 60/270,046 filed on Feb. 20, 2001.

The present invention relates to detectors of the type commonly referred to as electronic tongues, and in particular to an electronic tongue based on electrochemical detection, for the detection of the presence of ozone and measurement of its concentration in a liquid sample.

BACKGROUND OF THE INVENTION

The control of ozone levels in the ppm range is a very important tool i.a. for the sterilization of materials, e.g. preparations for medical use, equipment and apparatuses, where ozone is used for eliminating harmful and unwanted species. Ozone is a substance with excellent qualities to kill microbiological entities such as virus, bacteria, spores and fungi. As ozone is toxic to these entities already at low concentrations (ppm-range) it is imperative to be able to control and measure ozone on-line in real time. Such a method would be highly valuable for cleaning, disinfection and sterilization of various types of equipment and processes, such as medical devices, food and beverage processing equipment as well as in agriculture and breeding environments. The method could also be used for measuring the oxidation of organic material in the development and manufacturing of microelectronic products and production methods.

Ozone detectors according to prior art have been based on a number of different methods. Most methods require use of some kind of reagent, which means that either a sample must be withdrawn from the system in which the ozone is to be determined, or one has to accept a contamination of the system. The latter is unacceptable in e.g. sterilization of water for medical purposes. Spectroscopic methods would not cause such interferences, but requires fairly complex systems that are expensive. Also, they require the provision of windows in the light paths, where clogging can occur causing drift problems over time.

In WO 99/13325 there is disclosed an electronic tongue based on electrical pulses according to a pulse programme comprising a plurality of pulses in sequence and at different amplitudes, being applied to electrodes. The electrical pulses are i.a. selected from voltage pulses and current pulses. The obtained response signals are used as input to a pattern recognition program in a computer for interpretation and for outputting results indicative of a desired property of a sample, such as the concentration of an analyte, pH etc. The analysis is based on multivariate methods, such as PCA (Principal Component Analysis). A brief account of PCA is given in an article by F. Winquist et al in "An electronic tongue based on voltammetry", Analytica Chimica Acta, 357 (1997) 21–31. This article and the WO publication are both incorporated herein in their entirety by reference.

SUMMARY OF THE INVENTION

The present inventors have now conceived a new application of an electronic tongue of the type discussed above, namely for detection of the presence of and the measurement of the concentration of ozone in a liquid sample.

The invention in a first aspect comprises an electronic tongue for the detection of ozone, based on voltammetry, comprising at least one working electrode and a counter electrode, wherein the working electrode(s) is(are) made of one or more Rh, Pt, Au, Os, Ru, Ni, Ti, Re, or alloys thereof, or alloys thereof with other metals.

A system incorporating the inventive tongue comprises an ozone detection system based on voltammetry, for detecting the presence and/or concentration of ozone in a liquid sample, comprising at least one working electrode made of one or more transition metals or Au, or alloys thereof, or alloys thereof with other metals; a counter electrode; a programmable pulse generator capable of applying a redetermined sequence of energizing pulses to said working electrode(s); a recording device for recording the output from said working electrode generated in response to said applied pulse sequence; a sampling device for sampling values of said output at predetermined intervals; a memory for storing said sampled values in a matrix; a processing unit (PC) for performing a multivariate analysis of said data matrix; and a display device for displaying the result of said multivariate analysis.

The electronic tongue of the invention is based on voltammetry, and on a specific selection of metal(s) or metal alloys for the working electrode.

Advantages with the invention are i.a. the simplicity of the system, it is long term stable. In particular, it is possible to operate the system without a reference electrode. Thereby any risk of contamination of the system to be monitored with leaking electrolyte from a reference electrode is eliminated. Also, regular replacement of the reference electrode is eliminated.

Such replacement would otherwise have to be done at regular intervals, and adds further to the overall cost.

BRIEF DESCRIPTION OF THE DRAWINGS

The invention will be described in detain below with reference to the drawings, in which.

DETAILED DESCRIPTION OF PREFERRED EMBODIMENTS

For the purposes of the present invention the term "electronic tongue" shall be taken to mean a device comprising at least one sensing element, the response of which on stimulus from a sample is processed with multivariate methods. A "sensing element" can be any one of a plurality of devices, such as, but not limited to, electrodes at the surface of which redox reactions take place.

Figure 1:
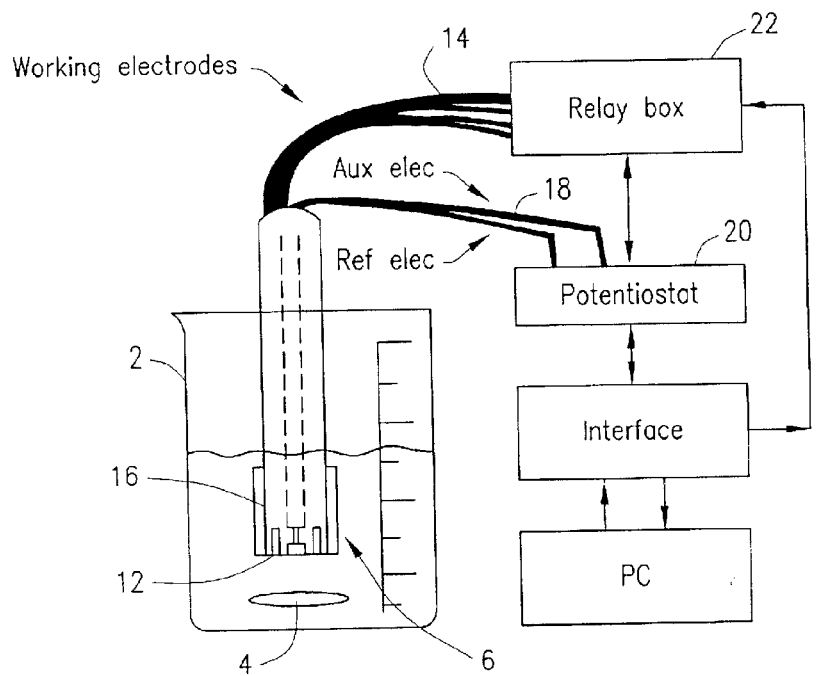
FIG. 1 shows a typical experimental setup for using the present invention.
Figure 2:
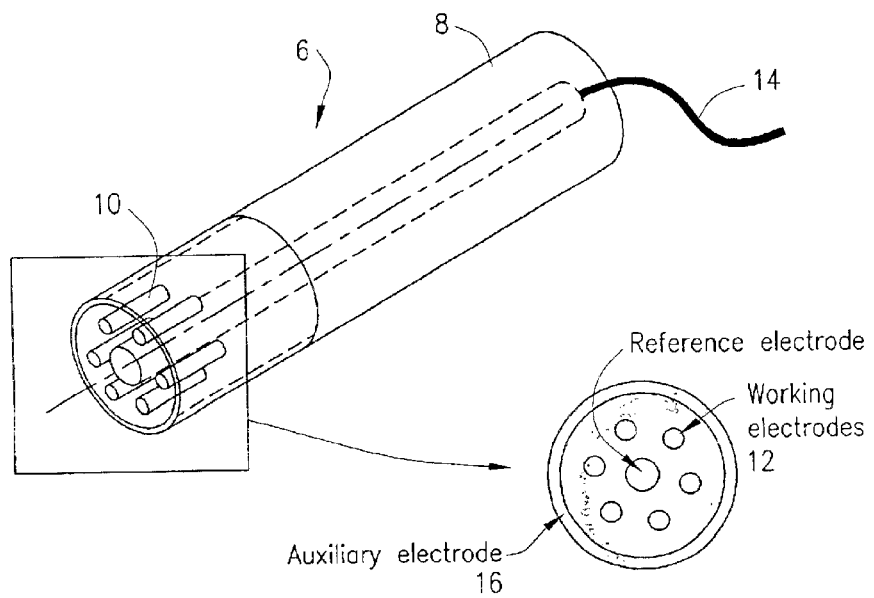
FIG. 2 shows an embodiment of a sensor device incorporating the inventive idea.

The invention will now be described with reference to one embodiment using a voltammetric system, and a setup of this type is shown in FIG. 1. The setup includes a sample reservoir 2 containing a sample, the ozone concentration of which is to be determined. This reservoir can be of a stationary type or designed as a flow cell, in the experiments described below a stationary cell with a magnetic stirrer 4 is used. A sensor device 6 is immersed in the sample liquid. The illustrated embodiment of the sensor device, shown in FIG. 2, comprises an essentially rod shaped support structure 8, in which a plurality of metal wires or metal pins 10 are imbedded, the ends of which are exposed. The exposed ends of the wires form the working electrodes 12 of the sensor device. The support structure is preferably made of a material that will ensure a very good sealing between the metal wires and the material in which they are embedded, in order to eliminate any interferences in the measurements due to liquid leaking in between the support material and the wire. A suitable material is a dental material, sold under the trade name Komposit™, Filtek™ Z250, obtainable from 3M Svenska AB, Sweden. Of course any other material having the capability to provide adequate sealing is usable.

An Ag/AgCl (KCl 3M) electrode can be used as a reference electrode, however other conventional reference electrode well known to the skilled man are equally well usable.

The measurement set up can be implemented in several ways. I.a. a standard three-electrode system can be employed, i.e. a working electrode, an auxiliary (counter) electrode and a reference electrode. Alternatively only a reference electrode and a working electrode can be used.

It should be noted however, that the invention works very well without the use of any reference electrode at all. Thus, in a preferred embodiment, a two-electrode set up with a working electrode and an auxiliary electrode is used. The potentials are controlled electronically and/or with software in the control unit (e.g. a potentiostat).

In the shown embodiment (FIG. 2) the sensor device comprises 6 working electrodes 12, made of different metals. However, the number of electrodes is not critical and could range from one single electrode up to several tens of electrodes or even more. The limit is in principle only set by the number of external connections to be made. It becomes increasingly difficult if several hundred electrodes are to be connected to external devices, although it should not be ruled out as a possibility. The metals from which the electrodes are made can be selected from one ore more members of the group consisting of Rh, Pt, Au, Os, Ru, Ni, Ti, Re and alloys thereof, or alloys thereof with other metals. Any metal that yields the desired effect would of course be applicable.

The metal wires extend throughout the support 8 and exits at the opposite end where they are connected to electrical leads 14. As an auxiliary electrode 16 (counter electrode) a tube of stainless steel encloses the rod shaped support structure in a tight fit. If the apparatus or system, in which the invention is implemented, is itself made of e.g. stainless steel, the apparatus housing could be used as a counter electrode. Other materials for the auxiliary electrode are of course conceivable, e.g. Pt, Au. An electrical lead 18 is connected also to the auxiliary electrode. The electrical leads from all electrodes are coupled to a potentiostat 20. The working electrodes are couple via a relay box 22 allowing each working electrode to be coupled separately in a two-electrode configuration (without reference), or three-electrode configuration (with reference).

Current and current transient responses are measured by a potentiostat MA 5410 (ISKRA, Chemel AB, Lund, Sweden) connected via an interface. An electronic filter with a time constant of 0.3 seconds is applied to the potentiostat in order to smooth the time transient responses. A personal computer is used for controlling the system, e.g. the timing of onset of pulses, operation of the relay box, measuring current transient responses and for the storage of data. A computer program written in Labview™ (National Instruments) is used to define the applied voltages on the electronic tongue, to control the sampling frequency and to define the data points to be stored in a data matrix.

Figure 3:
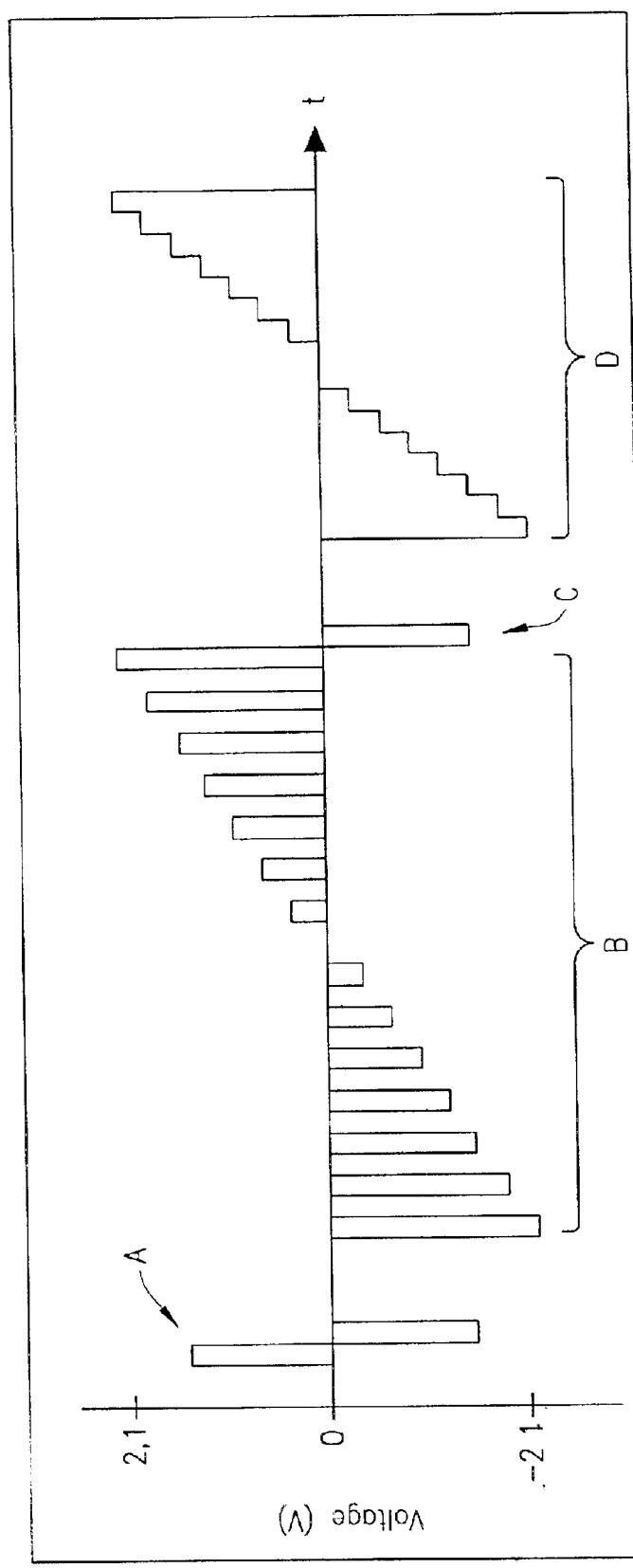
FIG. 3 shows a pulse sequence usable with the invention.

For the experiments that will be discussed below, a measurement sequence was composed with two types of voltages and two electrochemical cleaning procedures applied to the electronic tongue. Of course it should be realized that this is only an exemplary sequence, and virtually any combination of pulses (amplitude, duration etc) can be used, so long as a useful result can be obtained. Regarding the shape of pulses, there are many options available, e.g. square/rectangular pulses (as in the example below), sawtooth, sine wave, etc. Also, a four electrode (Au, Ir, Pt, Rh) sensor device was used. The sequence used in the experiments is as follows (illustrated in FIG. 3):

A: Electrochemical Cleaning

This procedure starts with a positive potential of 1.5 V applied to a working electrode during 0.5 s. Then a negative potential of 2.1 V is applied during 0.5 s. Finally the potential is set to 0 V during 2 s. This is repeated for all working electrodes.

B: Large Amplitude Pulse Voltammetry (LAPV)

The LAPV procedure starts with a potential of −2.1 V applied to a first working electrode during 0.5 s. The potential is then dropped to 0 V and maintained there for 0.5 s. Again a negative potential, but 300 mV higher than the first potential, is applied and maintained for 0.5 s, whereupon the potential again is set to 0 V. This sequence is continued until a final maximum potential of +2.1 V is reached.

C: Electrochemical Cleaning

The same procedure as in A is repeated.

D: Staircase Voltammetry

A potential of −2.1 V is applied to the working electrode, this potential is maintained for 0.5 s, and is then increased by 300 mV in steps until the final maximum potential of +2.1 V is reached.

This whole sequence A–D is repeated for each working electrode in the sensor device, i.e. four in the illustrated embodiment, and is defined as one cycle.

The measurement consists in sampling current values from the response curve generated as a result of the potential pulse programme. The measurement sequence is divided in 57 steps, each step having a duration of 500 ms. Current values are sampled at a rate of 1000 Hz, and thus each step generates 500 values, of which 19 are selected and stored in a data matrix. The selection of data points can be adapted to the specific case, and is not critical to the method. It is simply necessary to reduce the number of points to a reasonable number. However, a reasonable number can be very different from case to case. In certain cases perhaps it is sufficient with four points, in other circumstances of the order of 100 points could be relevant. Consequently, in the above example, for each electrode there will be 19×57=1083 values stored in the matrix, and totally for all four electrodes 4332 measurement values are generated and stored.

The data processing is done by multivariate analysis, in particular so-called Principal Component Analysis is used, and will be briefly discussed below, with reference to FIGS. 4–7.

Figure 4:
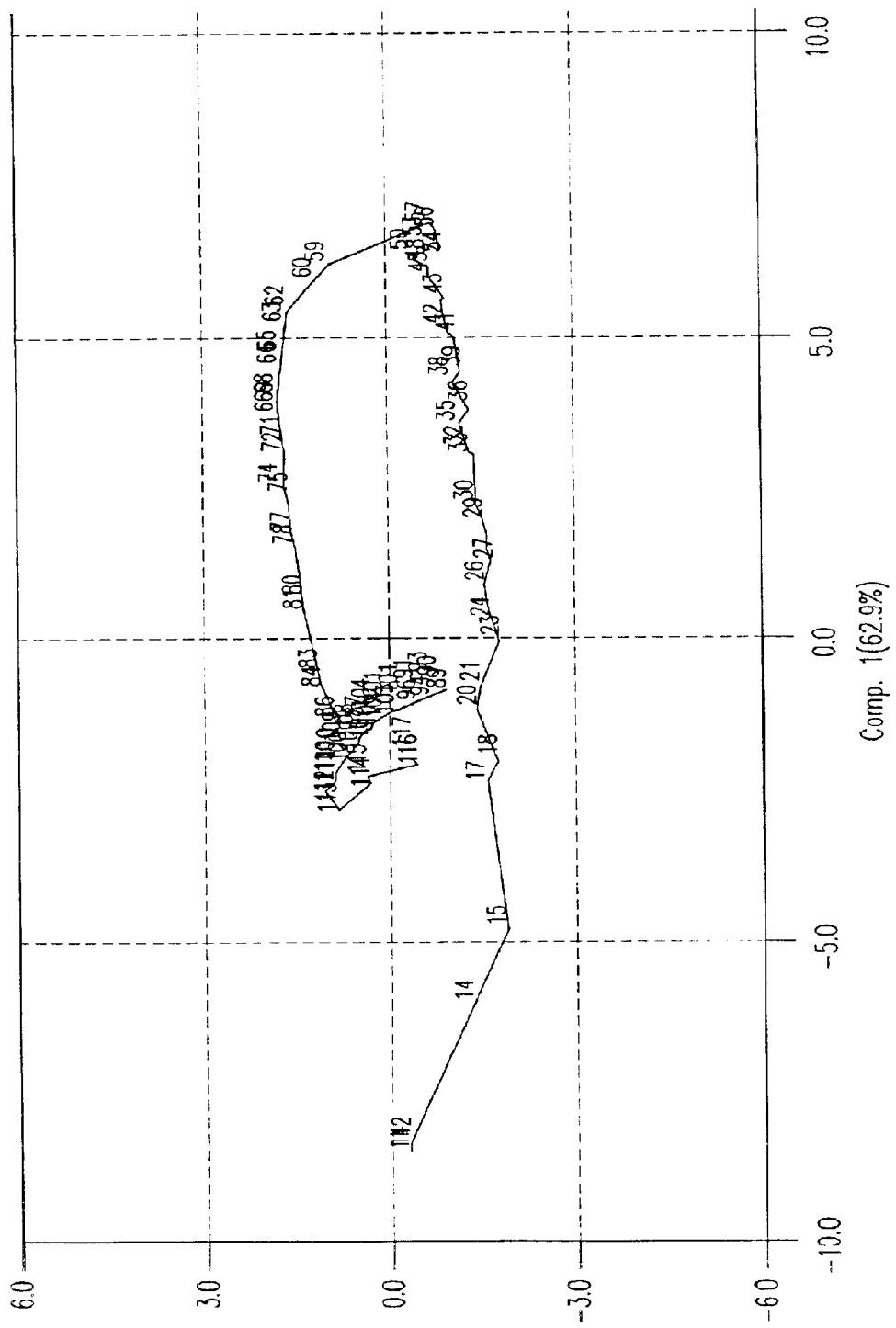
FIG. 4 is a PCA plot of a typical ozone measurement.

Thus, for the example given above where four different working electrodes are employed, a measurement consists of performing one pulse sequence for each electrode, which generates a data matrix with 4332 values. This matrix can be looked upon as one point in a 4332-dimensional space. Then, a new measurement is made, which generates a new matrix of 4332 values, and finally a set of matrices representing a number of points in 4332-dimensional space has been generated. In Table 1 a full data sampling experiment of 147 measurements is shown, and it will be discussed in some detail, and FIG. 4 is a graphical representation of the data in Table 1.

TABLE I

| Cycle | Conc. $O_3$ (ppm) | Temp °C. |
|---|---|---|
| 1 | 0 | 31 |
| 2 | 0 | 31 |
| 3 | 0 | 31 |
| 4 | 0 | 31 |
| 5 | 0 | 31 |
| 6 | 0 | 31 |
| 7 | 0 | 31 |
| 8 | 0 | 31 |
| 9 | 0 | 31 |
| 10 | 0 | 31 |
| 11 | 0 | 31 |
| 12 | 0 | 31 |
| 13 | 0.7–2.2 | 31 |
| 14 | 2.2–2.6 | 31 |
| 15 | 2.6–2.8 | 31 |
| 16 | 2.9 | 31 |
| 17 | 2.9 | 31 |
| 18 |  | 31 |
| 19 | 3.0–2.9 | 32 |
| 20 |  | 32 |
| 21 |  | 32 |
| 22 | 3.0–2.9 | 32 |
| 23 | 3.0–2.9 | 32 |
| 24 | 3.0–2.9 | 32 |
| 25 | 3.0–2.9 | 32 |
| 26 | 3.0–2.9 | 32 |
| 27 | 3.0–2.9 | 32 |
| 28 | 3.0–2.9 | 32 |
| 29 | 3.0–2.9 | 32 |
| 30 | 3.0–2.9 | 32 |
| 31 | 3.0–2.9 | 32 |
| 32 | 3.0–2.9 | 32 |
| 33 | 3.0–2.9 | 32 |
| 34 | 3.0–2.9 | 32 |
| 35 | 3.0–2.9 | 32 |
| 36 | 3.0–2.9 | 32 |
| 37 | 3.0–2.9 | 32 |
| 38 | 3.0–2.9 | 32 |
| 39 | 3.0–2.9 | 32 |
| 40 | 3.0–2.9 | 32 |
| 41 | 3.0–2.9 | 32 |
| 42 | 3.0–2.9 | 32 |
| 43 | 3.0–2.9 | 32 |
| 44 | 3.0–2.9 | 32 |
| 45 | 3.0–2.9 | 32 |
| 46 | 3.0–2.9 | 32 |
| 47 | 3.0–2.9 | 32 |
| 48 | 3.0–2.9 | 32 |
| 49 | 3.0–2.9 | 32 |
| 50 | 3.0–2.9 | 32 |
| 51 | 3.0–2.9 | 32 |
| 52 | 3.0–2.9 | 32 |
| 53 | 3.0–2.9 | 32 |
| 54 | 3.0–2.9 | 32 |
| 55 | 3.0–2.9 | 32 |
| 56 | 3.0–2.9 | 32 |
| 57 | 3.0–2.9 | 32 |
| 58 | 2.5–1.9 | 32 |
| 59 | 1.9–1.6 | 32 |
| 60 | 1.6–1.3 | 32 |
| 61 | 1.1–1.0 | 32 |
| 62 | 1.0–0.9 | 32 |
| 63 | 0.9–0.8 | 32 |
| 64 | 0.8–0.7 | 32 |
| 65 | 0.7 | 32 |
| 66 | 0.7–0.6 | 32 |
| 67 | 0.6–0.5 | 32 |
| 68 | 0.5 | 32 |
| 69 | 0.5 | 32 |
| 70 | 0.5–0.4 | 32 |
| 71 | 0.4 | 32 |
| 72 | 0.4–0.3 | 32 |
| 73 | 0.3 | 32 |
| 74 | 0.3 | 32 |
| 75 | 0.3–0.2 | 32 |
| 76 | 0.2 | 32 |
| 77 | 0.2 | 32 |
| 78 | 0.2–0.1 | 32 |
| 79 | 0.1 | 32 |
| 80 | 0.1–0 | 32 |
| 81 | 0.1–0 | 32 |
| 82 | 0 | 32 |
| 83 | 0 | 32 |
| 84 | 0 | 32 |
| 85 | 0 | 32 |
| 86 | 0 | 32 |
| 87 | 0 | 32 |
| 88 | 1.7–2.7 | 32 |
| 89 | 2.7–2.9 | 32 |
| 90 | 2.8–3.0 | 32 |
| 91 |  |  |
| 92 | 2.9–3.0 | 31 |
| 93 | 2.9–3.0 | 31 |
| 94 | 2.9–3.0 | 31 |
| 95 | 2.9–3.0 | 31 |
| 96 | 2.9–3.0 | 31 |
| 97 | 2.9–3.0 | 31 |
| 98 | 2.9–3.0 | 31 |
| 99 | 2.9–3.0 | 31 |
| 100 | 2.9–3.0 | 31 |
| 101 | 2.9–3.0 | 31 |
| 102 | 2.9–3.0 | 31 |
| 103 |  | 31 |
| 104 | 2.0 | 31 |
| 105 |  | 31 |
| 106 |  | 31 |
| 107 | 1.5 | 31 |
| 108 |  | 31 |
| 109 |  | 31 |
| 110 | 1.2 | 31 |
| 111 |  | 31 |
| 112 | 1.0 | 31 |
| 113 |  | 31 |
| 114 |  | 31 |
| 115 | 0.8 | 31 |
| 116 |  | 31 |
| 117 | 0.7 | 31 |
| 118 | 0.6 | 31 |
| 119 |  | 31 |
| 120 |  | 31 |
| 121 | 0.5 | 31 |
| 122 |  | 31 |
| 123 |  | 31 |
| 124 | 0.4 | 31 |
| 125 |  |  |
| 126 |  |  |
| 127 | 0.3 | 32 |
| 128 |  | 32 |
| 129 |  | 32 |
| 130 | 0.2 | 32 |

TABLE I-continued

| Cycle | Conc. O$_3$ (ppm) | Temp ° C. |
|---|---|---|
| 131 | | 32 |
| 132 | | 32 |
| 133 | 0.1 | 32 |
| 134 | | 32 |
| 135 | | 32 |
| 136 | 0.1 | 32 |
| 137 | 0.1–0 | 32 |
| 138 | | 32 |
| 139 | 0.1–0 | 32 |
| 140 | 0 | 32 |
| 141 | 0 | 32 |
| 142 | 0.8–0.9 | 32 |
| 143 | 0.9 | 32 |
| 144 | 0.9 | 32 |
| 145 | 2.4–2.9 | 32 |
| 146 | 2.9–3.0 | 32 |
| 147 | 2.9–3.0 | 32 |
| 148 | | |
| 149 | | |
| 150 | | |
| 151 | | |
| 152 | | |
| 153 | | |
| 154 | | |
| 155 | | |
| 156 | | |
| 157 | | |
| 158 | | |
| 159 | | |
| 160 | | |
| 161 | | |
| 162 | | |
| 163 | | |
| 164 | | |
| 165 | | |
| 166 | | |
| 167 | | |
| 168 | | |
| 169 | | |
| 170 | | |
| 171 | | |
| 172 | | |
| 173 | | |
| 174 | | |
| 175 | | |
| 176 | | |
| 177 | | |
| 178 | | |
| 179 | | |
| 180 | | |
| 181 | | |
| 182 | | |
| 183 | | |
| 184 | | |
| 185 | | |
| 186 | | |
| 187 | | |
| 188 | | |

Table 1 can be regarded as representing 147 points in 4332-dimensional space. Applying PCA to the data involves finding the direction in this space where the variance in the data is the largest. This will be a vector, called the fist principal component PC1, in the 4332-dimensional space. Subsequently the largest variance in a direction orthogonal to the first principal component, which of course also is a vector, called the second principal component PC2 (further principal components can be calculated, until most observations are explained).

A new matrix, as defined by the principal components, is then formed, and the data set is considerably reduced, depending on the significance of the principal components. In many cases the reduction will be only to two dimensions.

Thus, the two vectors, PC1 and PC2, define a two-dimensional plane which maximizes the variation in the original observations. The 147 points in 4332-dimensional space are now projected down onto the plane spanned by PC1 and PC2. Thereby the graph shown in FIG. 4 is generated.

During the sequence of measurements, the system is changed in terms of concentration of ozone, either by actively increasing the concentration with an ozone generator, or letting the concentration decay by decomposition of ozone over time. Table 1 clearly illustrates the changes. Thus, in cycles #1–12 the concentration was 0 ppm, in #13–18 it was gradually increased and maintained at approx. 3 ppm during cycles 22–57. Then the concentration was allowed to decay in cycles #58–81 down to 0 ppm during cycles #82–87. Again an increase in the concentration was performed in cycles #88–91 up to approx. 3 ppm during cycles #92–102, followed by a decay (#103–139). An increase of the concentration was brought about in #142–147.

As can be seen the measurements can be subdivided into groups relating to different states of the system, such as different concentrations, concentration decay periods, etc. The measurements on which the graph of FIG. 4 is based, are used to build a model for the data analysis with respect to the ozone concentration. When this model is applied to a set of measurements on a system with unknown ozone concentration, a prediction of the concentrations can be made.

Figure 5:
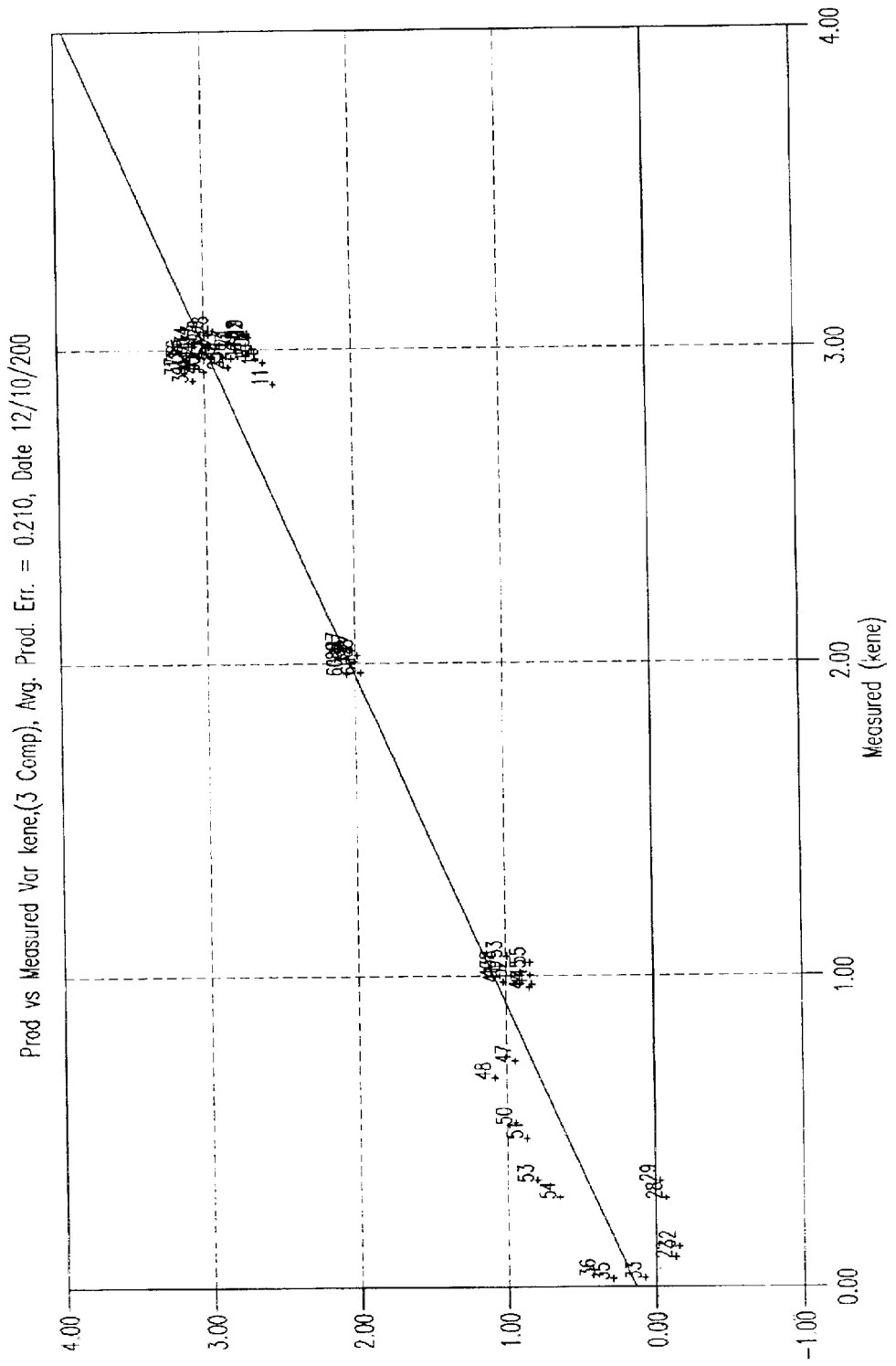
FIG. 5 shows correlation between measured and predicted concentration values determined according to the invention.
Figure 6A:
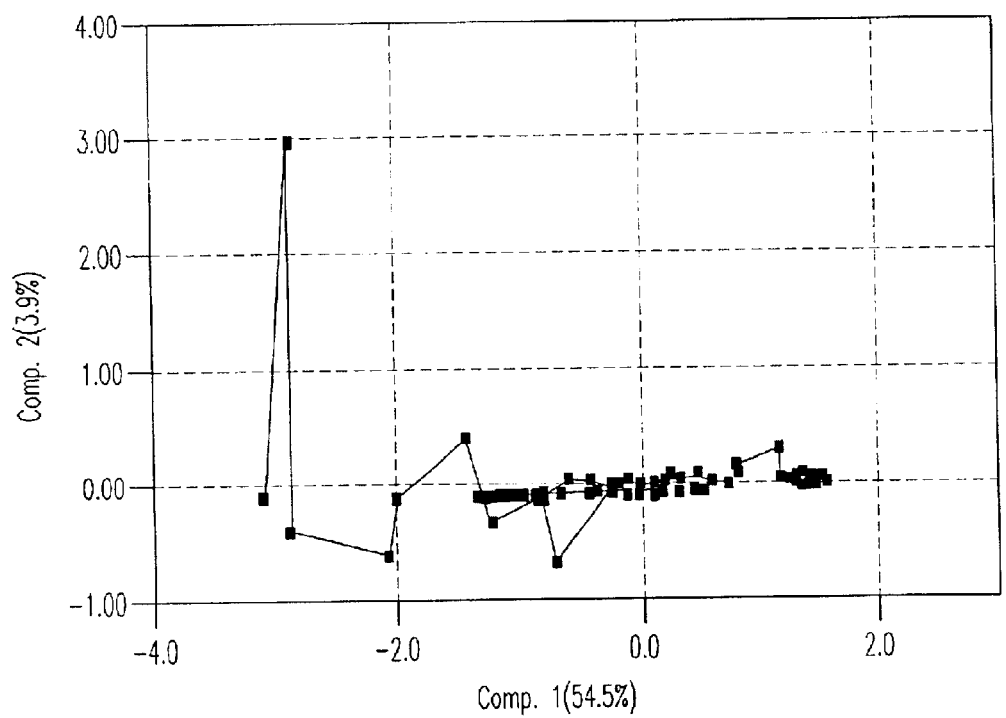
FIGS. 6a–d are PCA plots of measurements made with different single electrodes.
Figure 6B:
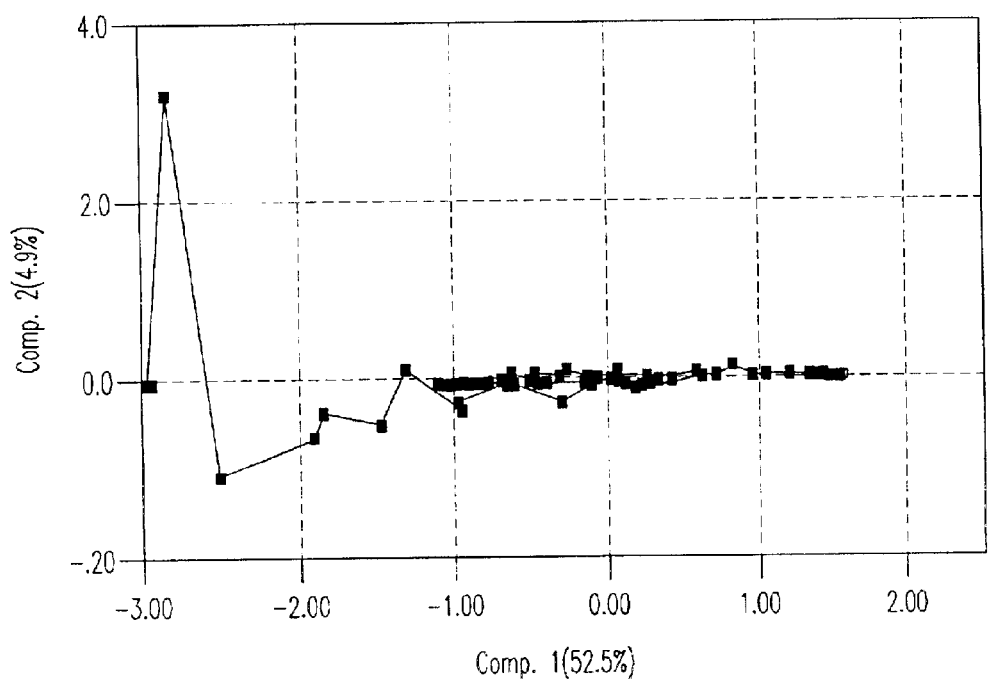
Figure 6C:
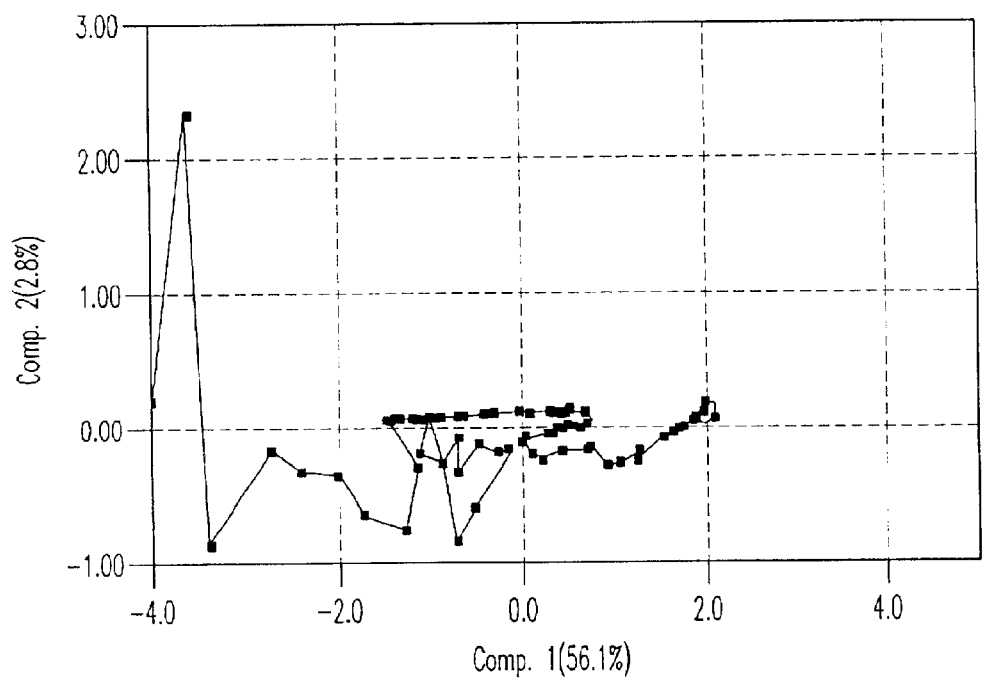
Figure 6D:
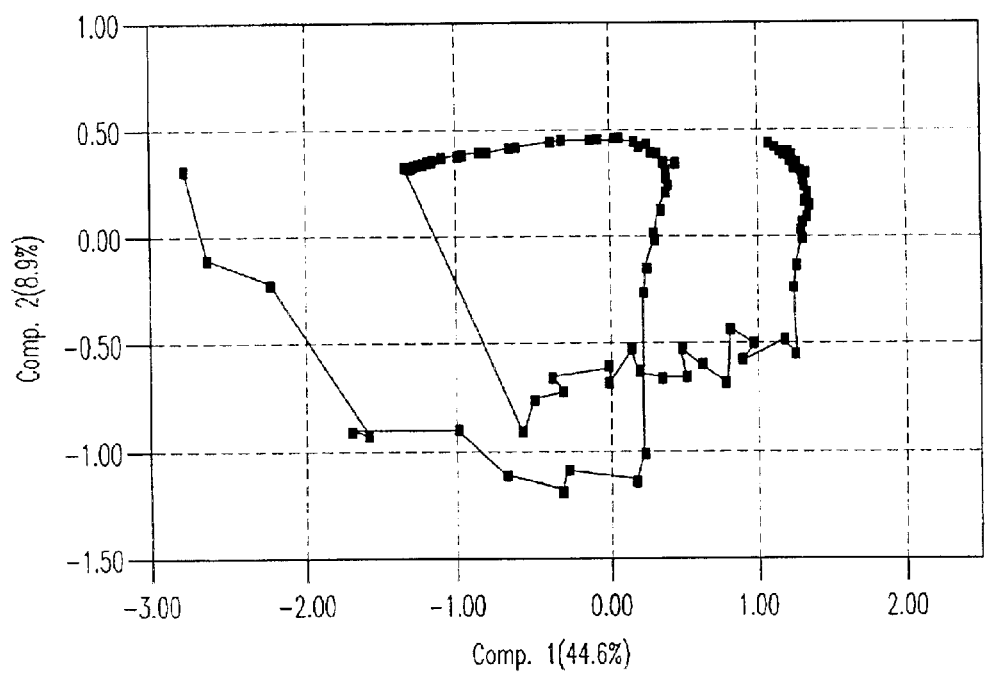

In order to validate that the model holds, a plot of predicted values vs. known values is made. Such a plot is shown in FIG. 5. As can be seen the correlation is very good. In FIGS. 6a–d a set of measurements represented by PCA plots, using the pulse sequence A–D above, on individual electrodes of four different metals (Au, Pt, Ir, Rh) is shown, and will be briefly discussed below.

As is clearly seen, there are qualitative differences between the experiments, the most obvious being that the graph representing Rh (FIG. 6d) has a significantly larger variation in the Y direction than the others. This variation can be used for modeling purposes and in particular it is applied to the determination of ozone concentration.

Figure 7:
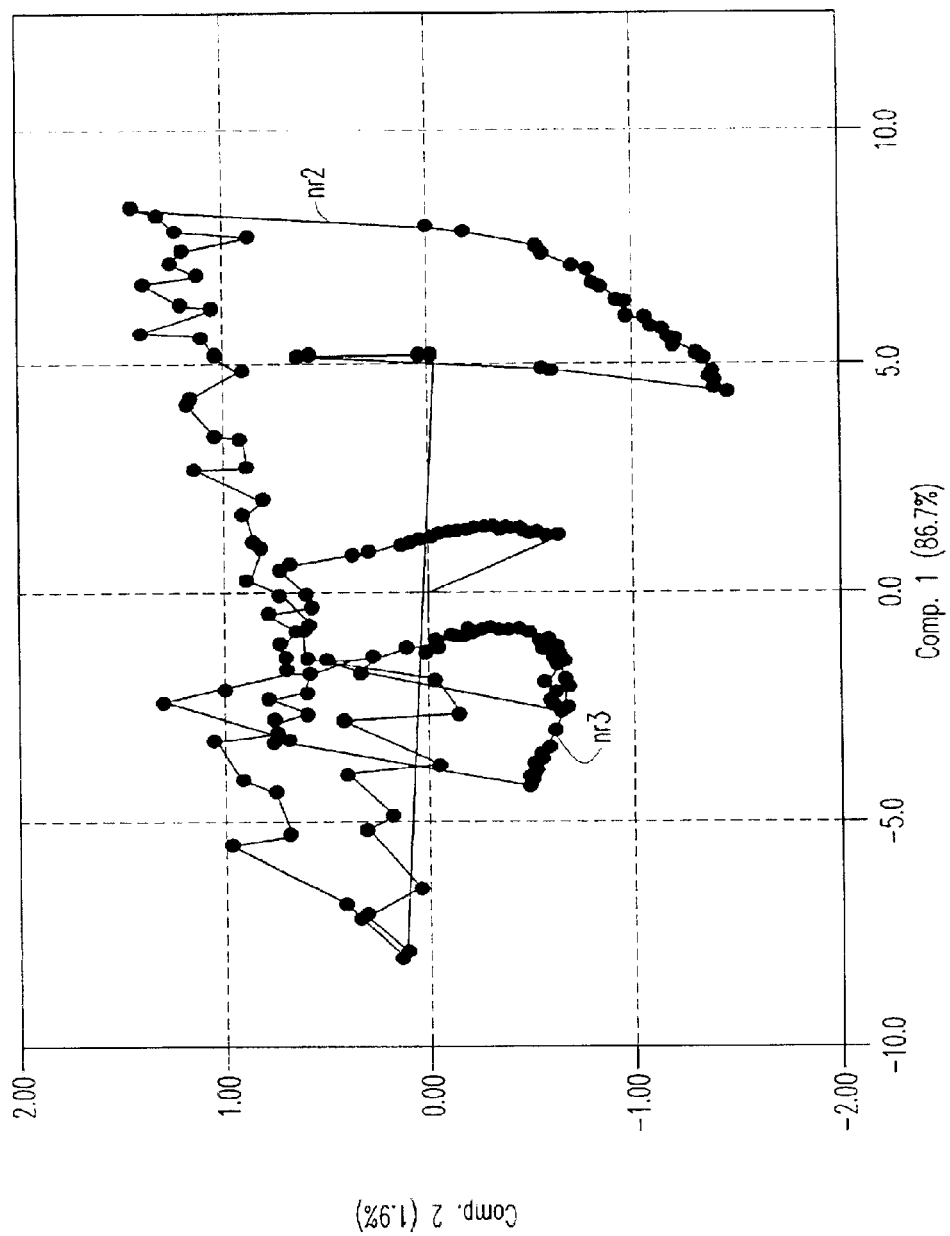
FIG. 7 is a PCA plot of a measurement based on a four-electrode sensor with different metals as electrodes.

In a further experiment illustrated by FIG. 7, the graph contains data from measurements of all four electrodes. It can be seen that the electrode made of Rh is a major contributor to the curve.

If a model is made on the basis of "training data", and a sensor with four different metals is used for measurements, it turns out that although the contribution from the less "ozone specific" metals (Au, Ir, Pt in the example above) is small, it turns out that the overall performance of the four electrode sensor is better than a sensor with a single electrode of Rh. This better performance is reflected in a better correlation coefficient in a corresponding PLS plot. An explanation is that in the data reduction process inherent in PCA, any "white nose" in the data does not contribute, but instead any significant information, regardless of its magnitude will have a positive contribution, and the final result will therefore be improved.

In the measurements discussed above, the potential in the pulse sequence was varied between −2.1 V and +2.1 V. However, it is possible to select other intervals for the measurements, and it is possible that one can optimize the sweep interval. In particular it is possible that it could be sufficient to work in only the negative range, e.g. 0 to −3.0 V, since the redox potentials for the possible reactions involving ozone are on the negative side.

It has turned out that the conductivity is relatively important for the quality of the results, in that the higher the conductivity is, the better the measurements will be. Therefore it can be desirable to measure the conductivity in order to be able to adjust it by adding ionic species, where the system so allows. For a closed in-line system it would mostly not be possible, and sometimes undesirable, in particular in systems for sterilization. For the conductivity measurements, two extra electrodes can be provided on the same support in the vicinity of the working electrodes of the electronic tongue.

Figure 8:
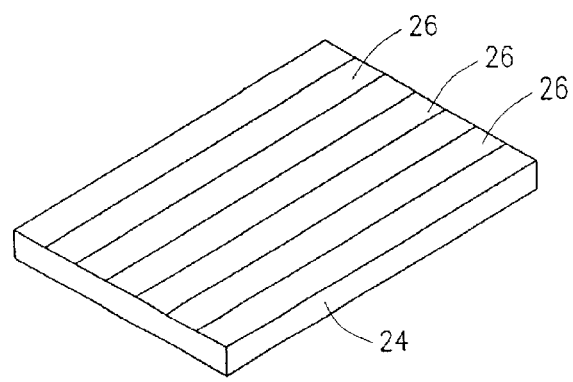
FIG. 8 shows an alternative embodiment of a sensor according to the invention.

The embodiment of the sensor device as discussed above is only one of many configurations possible for the working electrodes. Another way to make a device having a plurality of electrodes is schematically illustrated in FIG. 8, and is obtained by providing a plate like planar support member 24 of ceramic or other inert material, on which parallel strips 26 of different metals have been deposited. If one edge of the plate is immersed in a medium containing ozone such that a portion of each metal strip is in contact with the medium, the other end of each strip can be coupled to a potentiostat, in a similar way as indicated above for the rod shaped sensor device.

Figure 9:
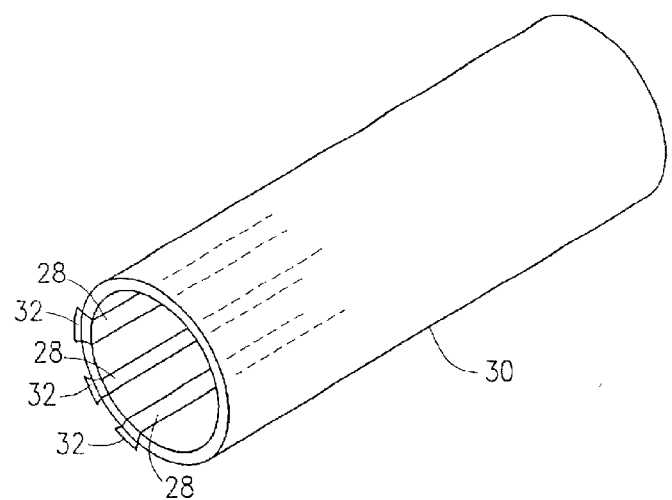
FIG. 9 shows still another embodiment of a sensor according to the invention.

Still another design of a sensor device, schematically shown in FIG. 9, is to integrate electrode strips 28 in the walls of a tubing segment 30 as part of a circulation conduit for e.g. a sterilization process. The metal strips could be inset in the wall of a special tube segment and having electrical through-connections 32 at least at one end of each metal strip, in order to provide for connection to suitable peripheral equipment, such as a potentiostat.

The skilled man could envisage several other variations and modifications of the actual arrangement and configuration of electrodes for a sensor device according to the present invention, all of which are intended to fall within the scope of the attached claims.

Figure 10:
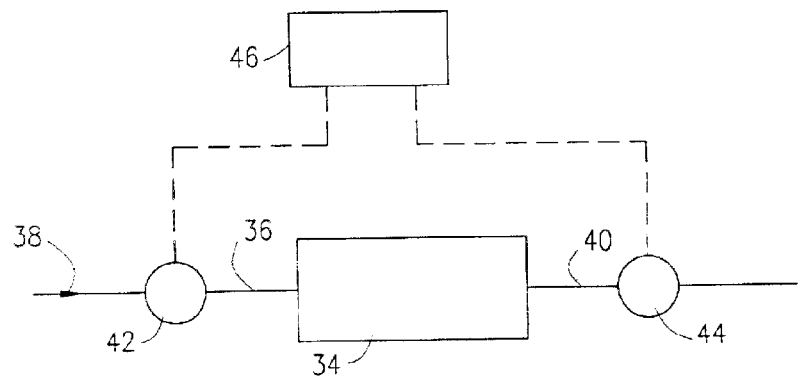
FIG. 10 schematically illustrates an implementation of an inventive sensor in a sterilization equipment.

A great advantage of the detector and measurement system according to the present invention is that it is suitable for on-line measurements of ozone in e.g. sterilization or purification equipment, where it is required that contamination is prevented. In FIG. 10 a schematic illustration of such an application is shown.

Thus, the illustrated system for purification comprises a treatment chamber 34, which can be a chamber containing utensils, such as surgical instruments, to be sterilized, or in itself can comprise an apparatus, such as a dialysis apparatus or the like. A feed conduit 36 having an inlet is 38 sealingly connected to the chamber. An outlet conduit 40 transports the used ozone-containing gas or liquid to disposal. It could of course in certain applications be recirculated back to the feed conduit (not shown). Ozone sensors 42, 44 according to the invention A control unit 46 can be coupled so as to control the sensors and in response to their outputs determine when a desired degree of e.g. sterilization has been achieved, and if desired, to regulate the level of ozone in the feed.

Thus, as shown, the invention can be implemented as a detection system for ozone, preferably on-line or in-line in the circulation system for the liquid, the ozone concentration of which it is desirable to monitor. Such a system would be based on voltammetry and comprises at least one working electrode made of a material as indicated above under the discussion of the sensor device, and a counter electrode. The electrodes are coupled to a programmable pulse generator capable of applying a predetermined sequence of energizing pulses to said working electrode(s), one at a time. The system further comprises a recording device for recording the output from said working electrode generated in response to said applied pulse sequence. A sampling device is provided for sampling values of said output at predetermined intervals, and the sampled values are stored in a memory in a matrix. There is a processing unit for performing a multivariate analysis of said data matrix, and a display device for displaying the result of said multivariate analysis.

Below a number of examples of measurements with different electronic tongues will be given with reference to tables and graphs.

Calibration Curves

To study the drift in the built-in amperometric sensor in the ozone generator 13 calibration experiments were performed during this work. Three (four for calibration curve 1) separate measurements formed the basis of one calibration curve. A multipoint working curve with 3 repetitions and a wavelength of 260 nm were chosen. The standard samples consisted of deionized water with the ozone concentrations 1, 1,5, 2, and 3 ppm. As reference solution deionized water was used. See Tables and graphs below for detailed information.

Record for Measurements with Spectophotometry

| Calibration curve No. 1, 000829 | | | | | |
|---|---|---|---|---|---|
| Conc $O_3$ (ppm) | 1 Abs | 2 Abs | 3 Abs | 4 Abs | MW Abs |
| 1 | 0.066 | 0.059 | 0.06 | 0.065 | 0.063 |
| 1.5 | 0.091 | 0.084 | 0.09 | 0.087 | 0.088 |
| 2 | 0.128 | 0.113 | 0.113 | 0.13 | 0.121 |
| 3 | 0.186 | 0.164 | 0.164 | 0.191 | 0.176 | y = 0.059x + 0.0028
Correlation coefficient = 99.73%

| Calibration curve No. 2, 000925 | | | | |
|---|---|---|---|---|
| Conc $O_3$ (ppm) | 1 Abs | 2 Abs | 3 Abs | MW Abs |
| 1 | 0.061 | 0.064 | 0.06 | 0.063 |
| 1.5 | 0.094 | 0.087 | 0.091 | 0.088 |
| 2 | 0.112 | 0.122 | 0.118 | 0.121 |
| 3 | 0.156 | 0.180 | 0.194 | 0.176 | y = 0.057x + 0.0048
Correlation coefficient = 99.99%

| Calibration curve No. 3, 001011 | | | | |
|---|---|---|---|---|
| Conc $O_3$ (ppm) | 1 Abs | 2 Abs | 3 Abs | MW Abs |
| 1 | 0.07 | 0.057 | 0.059 | 0.062 |
| 1.5 | 0.108 | 0.094 | 0.099 | 0.1 |
| 2 | 0.126 | 0.137 | 0.136 | 0.133 |
| 3 | 0.203 | 0.196 | 0.189 | 0.196 | y = 0.066x + 0.0017
Correlation coefficient = 99.90%

| Calibration curve No. 4, 001108 | | | | |
|---|---|---|---|---|
| Conc $O_3$ (ppm) | 1 Abs | 2 Abs | 3 Abs | MW Abs |
| 1 | 0.068 | 0.068 | 0.063 | 0.066 |
| 1.5 | 0.102 | 0.102 | 0.096 | 0.1 |

-continued

| Calibration curve No. 4, 001108 | | | | |
|---|---|---|---|---|
| Conc O$_3$ (ppm) | 1 Abs | 2 Abs | 3 Abs | MW Abs |
| 2 | 0.125 | 0.126 | 0.124 | 0.125 |
| 3 | 0.181 | 0.195 | 0.181 | 0.186 | y = 0.059x + 0.0087
Correlation coefficient = 99.92%

| Calibration curve No. 5, 001206 | | | | |
|---|---|---|---|---|
| Conc O$_3$ (ppm) | 1 Abs | 2 Abs | 3 Abs | MW Abs |
| 1 | 0.071 | 0.064 | 0.076 | 0.070 |
| 1.5 | 0.088 | 0.091 | 0.091 | 0.09 |
| 2 | 0.114 | 0.123 | 0.124 | 0.120 |
| 3 | 0.166 | 0.168 | 0.180 | 0.171 | y = 0.051x + 0.017
Correlation coefficient = 99.83%

Figure 11:
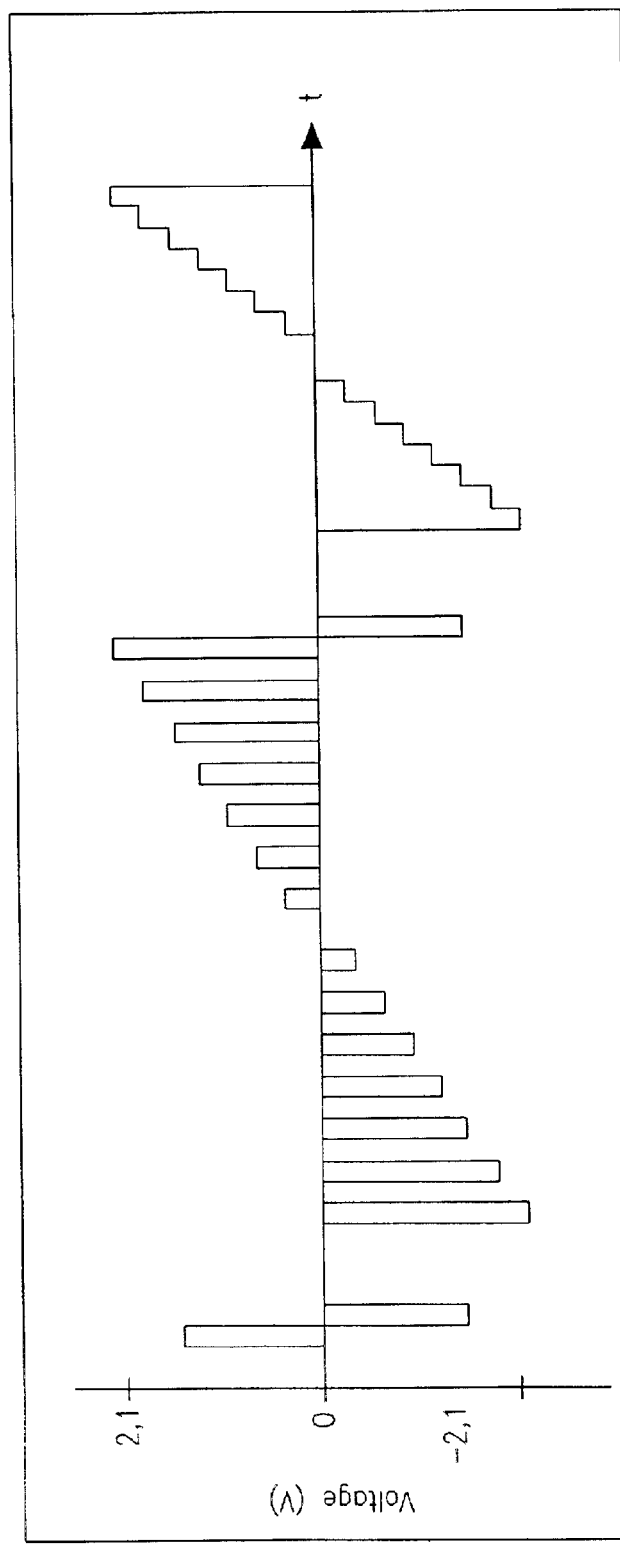
FIG. 11 is a schematic illustration of a LAPV stair case.

A measurement sequence (see FIG. 11) was composed (Labview from National Instruments) of two types of voltages and two electrochemical cleaning procedures applied to the electronic tongue in the following order:

1) Electrochemical Cleaning Procedure

The electrochemical cleaning procedure of the electrode starts with a positive voltage of 1.5 V during 0.5 s. Then a negative potential of 1.5 V is applied for the same time. Thereafter the voltage Is set to 0 V for 2 s.

2) LAPV

The LAPV starts with a potential of −2.1 V, then the voltage is set to 0 V. Then the potential is increased by 300 mV and the sequence starts all over again. This continues until the voltage reaches a final maximum potential of +2.1 V.

3) Electrochemical Cleaning Procedure

See 1) above.

4) Staircase

The voltage starts at −2.1 V and is then increased by 300 mV until the final maximum potential is reached.

The measurement sequence is applied first to the gold wire, followed by the wires of iridum, platinum, and rhodium, which define a cycle. The measurement sequence was divided in 57 steps, each with a step time of 500 ms. Current values are sampled with a sample frequency of 1000 Hz. Each step generates 500 sample values (keys) of which nineteen are stored in the data matrix. On each working electrode 19×57=1083 values are stored in the data matrix. From all four working electrodes, 4×1083=4332 measurement values are generated. The applied potentials, the sampling frequency and the data points that are chosen can be seen in the table below.

Configuration for Electronic Tongue Measurement

No. Cycles: 200

Time between cycles: 0 min

No. Propes: 4

Sample/Step: 495

Aq Rate: 1000 samples/s

No. Steps: 57

Step time: 500 ms

No. Keys: 19

Data point/row: 4332

| Output data | Output data | Keys |
|---|---|---|
| 1.500 | 1.500 | 25 |
| −1.500 | 0.000 | 50 |
| 0.000 | 1.800 | 75 |
| 0.000 | 0.000 | 100 |
| 0.000 | 2.100 | 125 |
| 0.000 | −1.500 | 150 |
| −2.100 | 0.000 | 175 |
| 0.000 | 0.000 | 200 |
| −1.900 | 0.000 | 225 |
| 0.000 | 0.000 | 250 |
| −1.500 | −2.100 | 275 |
| 0.000 | −1.800 | 300 |
| −1.200 | −1.500 | 325 |
| 0.000 | −1.200 | 350 |
| −0.900 | −0.900 | 375 |
| 0.000 | −0.600 | 400 |
| −0.600 | −0.300 | 425 |
| 0.000 | 0.000 | 450 |
| −0.300 | 0.000 | 475 |
| 0.000 | 0.300 | |
| 0.000 | 0.600 | |
| 0.300 | 0.900 | |
| 0.000 | 1.200 | |
| 0.600 | 1.500 | |
| 0.000 | 1.800 | |
| 0.900 | 2.100 | |
| 1.200 | 0.000 | |
| 0.000 | 0.000 | |

During the experiments the ozone concentration was manually varied from 0–3 ppm in the six opening experiments. Thereafter an automatic program for changing the ozone concentration was used. The ozone concentration and the corresponding temperature were recorded manually respectively automatically for each cycle during the measurements.

In the six opening experiments the impact of a cold respectively warm ozone generator, water quality, old respectively new packing and conductivity were studied. See the table below for experiment data. For more detailed experiment data see the tables below, and FIGS. 12–18.

Figure 12:
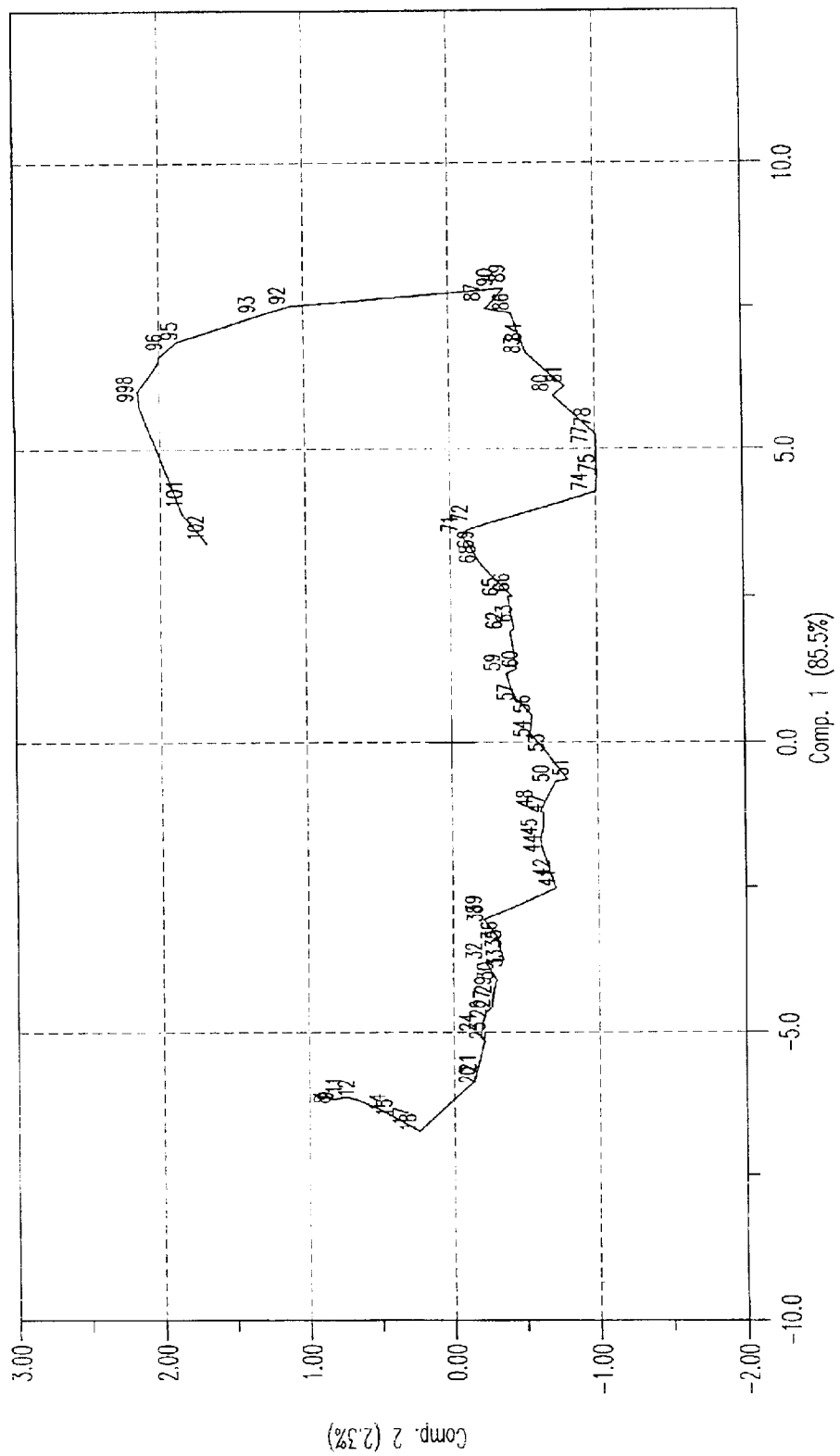
FIGS. 12–18 are graphs showing measurements with a number of electronic tongues.

Record for Measurement with the Electronic Tongue 000919 (FIG. 12)

New deionized water (just before start), packing ring nr 1 and a cold ozone generator are used for experiment 1.

| Cycle | Conc O$_3$ (ppm) | Temp ° C. |
|---|---|---|
| 1 | 1 | 20 |
| 2 | 0 | 20 |
| 3 | 0 | 20 |
| 4 | 0 | 21 |
| 5 | 0 | 21 |
| 6 | 0 | 21 |
| 7 | 0 | 21 |
| 8 | 0 | 21 |
| 9 | 0 | 21 |
| 10 | 0 | 22 |
| 11 | 0 | 22 |
| 12 | 0 | 22 |
| 13 | 0 | 22 |
| 14 | 0 | 22 |
| 15 | 0 | 22 |
| 16 | 0 | 23 |
| 17 | 0 | 23 |
| 18* | 0 | 23 |
| 19 | 1.4–1.7 | 23 |
| 20 | 1.7–1.6 | 23 |

-continued

| Cycle | Conc O₃ (ppm) | Temp ° C. |
|---|---|---|
| 21 | 1.6–1.4 | 23 |
| 22 | 1.2–1.1 | 23 |
| 23 | 1.1–1.0 | 23.5 |
| 24 | 1.0–1.1 | 24 |
| 25 | 1.0–0.9 | 24 |
| 26 | 0.9 | 24 |
| 27 | 0.9–1.0 | 24 |
| 28 | 1.0 | 24 |
| 29 | 1.0 | 24 |
| 30 | 1.0 | 24 |
| 31 | 1.0 | 24 |
| 32 | 1.0–0.9 | 24.5 |
| 33 | 1.0 | 25 |
| 34 | 1.0–1.1 | 25 |
| 35 | 1.0–0.9 | 25 |
| 36 | 0.9–1.0 | 25 |
| 37 | 0.9–1.0 | 25 |
| 38 | 0.9–1.0 | 25 |
| 39* | 0.9–1.0 | 25 |
| 40 | 1.9–2.0 | 25 |
| 41 | 2.0–1.9 | 25 |
| 42 | 1.9–2.0 | 25 |
| 43 | 2.0 | 25 |
| 44 | 2.0–1.9 | 25 |
| 45 | 1.9 | 25 |
| 46 | 2.0–1.9 | 25 |
| 47 | 2.0–1.9 | 25 |
| 48 | 2.0–1.9 | 25 |
| 49 | 1.9–2.0 | 25 |
| 50 | 1.9–2.0 | 25 |
| 51 | 2.0 | 25.5 |
| 52 | 1.9–2.0 | 26 |
| 53 | 1.9–2.0 | 26 |
| 54 | 1.9–2.0 | 26 |
| 55 | 1.9–2.0 | 26 |
| 56 | 1.9–2.0 | 26 |
| 57 | 1.9–2.0 | 26 |
| 58 | | |
| 59 | | |
| 61 | | |
| 62 | | |
| 63 | | |
| 64 | | |
| 65 | | |
| 66 | | |
| 67 | | |
| 68 | | |
| 69 | | |
| 70 | | |
| 71 | | |
| 72* | | |
| 73 | 2.9–3.0 | 31 |
| 74 | 2.9–3.0 | 31 |
| 75 | 2.9–3.0 | 31 |
| 76 | 2.9–3.0 | 31 |
| 77 | 2.9–3.0 | 31.5 |
| 78 | 2.9–3.0 | 32 |
| 79 | 3.0–3.0 | 32 |
| 80 | 3.0–3.0 | 32 |
| 81 | 3.0–3.0 | 32 |
| 82 | 3.0–3.0 | 32 |
| 83 | 3.0–3.0 | 32 |
| 84 | 3.0–3.0 | 32 |
| 85 | 3.0–3.0 | 32 |
| 86 | 2.9 | |
| 87 | 2.9 | 32 |
| 88 | 2.9–3.0 | 32 |
| 89 | 2.9–3.0 | 32 |
| 90* | 2.9 | 32 |
| 91 | 2.1–1.8 | 32 |
| 92 | 1.8–1.5 | 32 |
| 93 | 1.5–1.4 | 32 |
| 94 | 1.0–0.9 | 32 |
| 95 | 0.9–0.8 | 32 |
| 96 | 0.8–0.7 | 32 |
| 97 | 0.5–0.4 | 32 |

-continued

| Cycle | Conc O₃ (ppm) | Temp ° C. |
|---|---|---|
| 98 | 0.4–0.3 | 32 |
| 99 | 0.3–0.2 | 32 |
| 100 | 0.1–0 | 32 |
| 101 | 0 | 32 |
| 102 | 0 | 32 |

*The ozone concentration is changed manually after indicated cycle.
Every third cycle (1, 4, 7 etc.) and the data points from the electrochemical cleaning are excluded from the data analysis.

Figure 13:
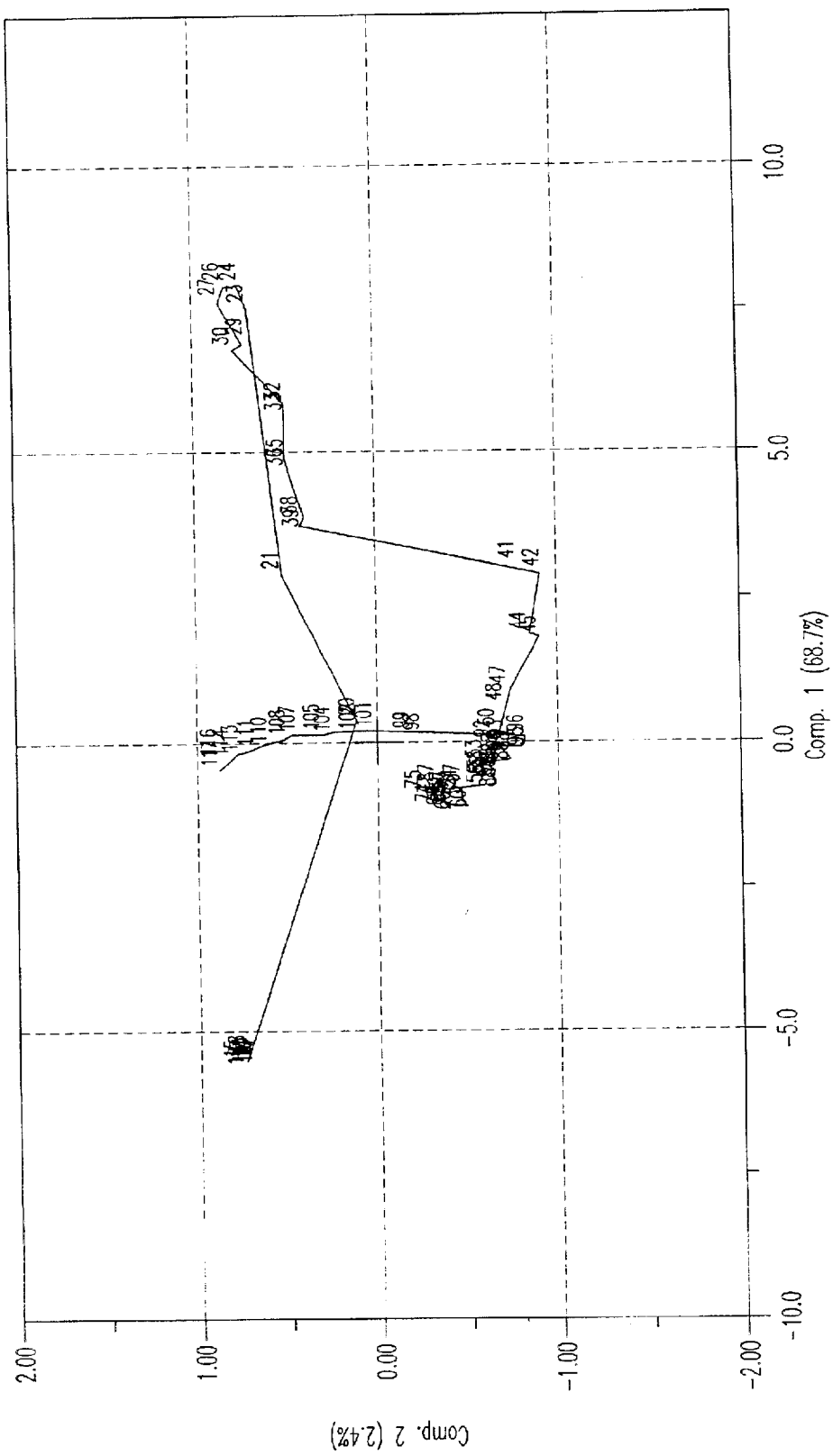
Figure 14:
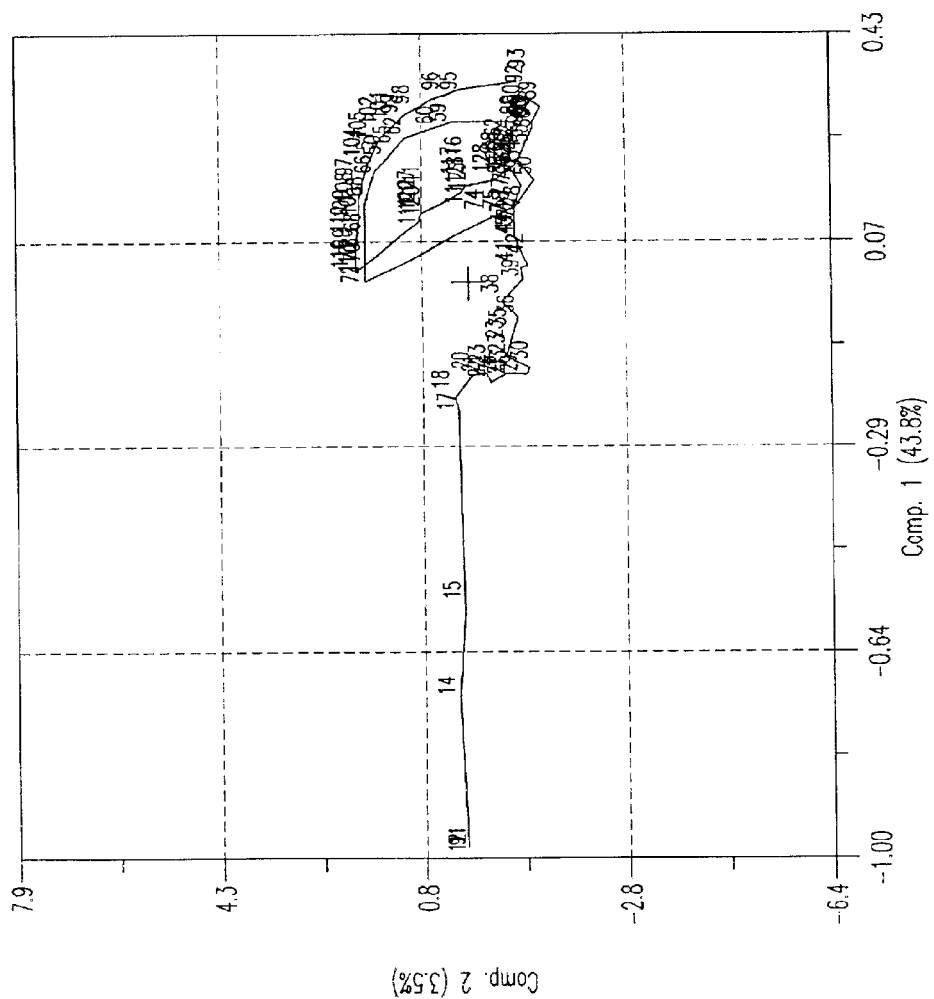

Record for Measurement with the Electronic Tongue 000920 (FIG. 13)

New deionized water (just before warming up), packing ring nr 1 and a warm ozone generator used for experiment 2.

| Cycle | Conc O₃ (ppm) | Temp ° C. |
|---|---|---|
| 1 | 0 | 33 |
| 2 | 0 | 33 |
| 3 | 0 | 33 |
| 4 | 0 | 33 |
| 5 | 0 | 33 |
| 6 | 0 | 33 |
| 7 | 0 | 33 |
| 8 | 0 | 33 |
| 9 | 0 | 33 |
| 10 | 0 | 33 |
| 11 | 0 | 33 |
| 12 | 0 | 33 |
| 13 | 0 | 33 |
| 14 | 0 | 33 |
| 15 | 0 | 33 |
| 16 | 0 | 33 |
| 17 | 0 | 33 |
| 18* | 0 | 33 |
| 19 | 0.5–0.8 | 33 |
| 20 | 0.8–0.9 | 33 |
| 21 | 0.9–1.0 | 33 |
| 22 | 0.9–1.0 | 33 |
| 23 | 1.0–0.9 | 33 |
| 24 | 1.0–0.9 | 32.5 |
| 25 | 1.0–0.9 | 32 |
| 26 | 0.9–1.0 | 32 |
| 27 | 0.9–1.0 | 32 |
| 28 | 0.9–1.0 | 32 |
| 29 | 0.9–1.0 | 32 |
| 30 | 0.9–1.0 | 32 |
| 31 | 0.9–1.0 | 32 |
| 32 | 0.9–1.0 | 32 |
| 33 | 1.0–0.9 | 32 |
| 34 | 0.9–1.0 | 32 |
| 35 | 0.9–1.0 | 32 |
| 36 | 0.9–1.0 | 32 |
| 37 | 0.9–1.0 | 32 |
| 38 | 0.9–1.0 | 32 |
| 39* | 0.9–1.0 | 32 |
| 40 | 1.9–2.0 | 32 |
| 41 | 1.9–2.0 | 32 |
| 42 | 1.9–2.0 | 32 |
| 43 | 0.9–2.0 | 32 |
| 44 | 0.9–2.0 | 32 |
| 45 | 0.9–2.1 | 32 |
| 46 | 2.0 | 32 |
| 47 | 2.0–1.9 | 32 |
| 48 | 1.9–2.0 | 32 |
| 49 | 1.9–2.0 | 32 |
| 50 | 2.0 | 32 |
| 51 | 2.0–1.9 | 32 |
| 52 | 2.0–1.9 | 32 |
| 53 | 2.0 | 32 |

-continued

| Cycle | Conc O₃ (ppm) | Temp °C. |
|---|---|---|
| 54 | 1.9–2.1 | 32 |
| 55 | 2.0 | 32 |
| 56 | 2.0 | 32 |
| 57 | 2.0 | 32 |
| 58 | | |
| 59 | | |
| 60 | | |
| 61 | | |
| 62 | | |
| 63 | | |
| 64 | | |
| 65 | | |
| 66 | | |
| 67 | | |
| 68 | | |
| 69 | | |
| 70 | | |
| 71 | | |
| 72 | | |
| 73 | | |
| 74 | | |
| 75 | | |
| 76 | | |
| 77 | | |
| 78* | | |
| 79 | 2.9–3.0 | 32 |
| 80 | 3.0 | 32 |
| 81 | 3.0–2.9 | 32 |
| 82 | 2.9–3.0 | 32 |
| 83 | 3.0–2.9 | 32 |
| 84 | 3.0–2.9 | 32 |
| 85 | 3.0–2.9 | 32 |
| 86 | 2.9–3.0 | 32 |
| 87 | 2.9–3.0 | 32 |
| 88 | 2.9–3.0 | 32 |
| 89 | 2.9–3.0 | 32 |
| 90 | 2.9–3.0 | 32 |
| 91 | 2.9–3.0 | 32 |
| 92 | 2.9–3.0 | |
| 93 | 2.9–3.0 | 31 |
| 94 | 2.9–3.0 | 31 |
| 95 | 2.9–3.0 | 31 |
| 96* | 2.9–3.0 | 31 |
| 97 | 2.3–2.1 | 31 |
| 98 | 2.1–1.8 | 31 |
| 99 | 1.8–1.6 | 31 |
| 100 | 1.3–1.2 | 31 |
| 101 | 1.2–1.1 | 31 |
| 102 | 1.1–1.0 | 31 |
| 103 | 0.8 | 31 |
| 104 | 0.8–0.7 | 31 |
| 105 | 0.7–0.6 | 31 |
| 106 | 0.5 | 31 |
| 107 | 0.5–0.4 | 31 |
| 108 | 0.4 | 31 |
| 109 | 0.3 | 31 |
| 110 | 0.3–0.2 | 31 |
| 111 | 0.2 | 31 |
| 112 | 0.1 | 31 |
| 113 | 0.1 | 31 |
| 114 | 0.1 | 31 |
| 115 | 0–0.1 | 31 |
| 116 | 0 | 31 |
| 117 | 0 | 31 |

*The ozone concentration is changed manually after indicated cycle.
Every third cycle (1, 4, 7 etc.) and the data points from the electrochemical cleaning are excluded from the data analysis.

Record for Measurement with the Electric Tongue 000926

New milli-q water (just before warming up and before start), packing ring nr 1 and a warm ozone generator are used for experiment 4.

| Cycle | Conc O₃ (ppm) | Temp °C. |
|---|---|---|
| 1 | 0 | 34 |
| 2 | 0 | 34 |
| 3 | 0 | 34 |
| 4 | 0 | 34 |
| 5 | 0 | 34 |
| 6 | 0 | 34 |
| 7 | 0 | 34 |
| 8 | 0 | 34 |
| 9 | 0 | 34 |
| 10 | 0 | 34 |
| 11 | 0 | 34 |
| 12* | 0 | 34 |
| 13 | 0–0.5 | 33.5 |
| 14 | 0.5–1.0 | 33 |
| 15 | 1.0–1.6 | 33 |
| 16 | 2.0–2.3 | 33 |
| 17 | 2.3 | 33 |
| 18 | 2.3–2.4 | 33 |
| 19 | 2.4–2.5 | 33 |
| 20 | 2.5 | 33 |
| 21 | 2.6 | 33 |
| 22 | | |
| 23 | 2.7 | 33 |
| 24 | 2.7 | 33 |
| 25 | | |
| 26 | | |
| 27 | | |
| 28 | | |
| 29 | | |
| 30 | | |
| 31 | | |
| 32 | | |
| 33 | | |
| 34 | | |
| 35 | | |
| 36 | | |
| 37 | | |
| 38 | | |
| 39 | | |
| 40 | | |
| 41 | | |
| 42 | | |
| 43 | | |
| 44 | | |
| 45 | | |
| 46 | | |
| 47 | | |
| 48 | | |
| 49 | | |
| 50 | | |
| 51 | | |
| 52 | | |
| 53 | | |
| 54 | | |
| 55 | | |
| 56 | | 32 |
| 57* | | 32 |
| 58 | 2.6 | 32 |
| 59 | | |
| 60 | | |
| 61 | | |
| 62 | | |
| 63 | | |
| 64 | | |
| 65 | | |
| 66 | | |
| 67 | | |
| 68 | | |
| 69 | | |
| 71 | | |
| 72* | 0 | 32 |
| 73 | | |
| 74 | | |
| 75 | 2.9 | 32 |
| 76 | | |
| 77 | | |

-continued

| Cycle | Conc $O_3$ (ppm) | Temp ° C. |
|---|---|---|
| 78 | | |
| 79 | | |
| 80 | | |
| 81 | | |
| 82 | | |
| 83 | | |
| 84 | | |
| 85 | | |
| 86 | | |
| 87 | | |
| 88 | | |
| 89 | | |
| 90 | | |
| 91 | | |
| 92 | | |
| 93 | 2.9–3.0 | 32 |
| 94 | 2.5–2.1 | 32 |
| 95 | 2.1–1.6 | 32 |
| 96 | 1.6–1.3 | 32 |
| 97 | 1.0–0.8 | 32 |
| 98 | 0.8–0.7 | 32 |
| 99 | 0.7–0.6 | 32 |
| 100 | 0.5 | 32 |
| 101 | 0.4 | 32 |
| 102 | 0.4–0.3 | 32 |
| 103 | 0,3–0.2 | 32 |
| 104 | 0.2–0.1 | 32 |
| 105 | 0.1 | 32 |
| 106 | 0.1–0 | 32 |
| 107 | 0 | 32 |
| 108 | 0 | 32 |
| 109 | 0 | 32 |
| 110 | 0 | 32 |
| 111 | 0 | 32 |
| 112 | 0 | 32 |
| 113 | 0 | 32 |
| 114* | 0 | 32 |
| 115 | 0.7–0.9 | 32 |
| 116 | 0.9–1.0 | 32 |
| 117 | 0.9–1.0 | 32 |
| 118 | 0.9–1.0 | 32 |
| 119 | 1.0 | 32 |
| 120* | 1.0 | 32 |
| 121 | 1.0–1.8 | 32 |
| 122 | 1.8–2.0 | 32 |
| 123 | 1.9–2.0 | 32 |
| 124 | 1.9–2.0 | 32 |
| 125 | 1.9–2.0 | 32 |
| 126* | 1.9–2.0 | 32 |
| 127 | 2.8–2.9 | 32 |
| 128 | 2.9–3.0 | 32 |
| 129 | 2.9–3.0 | 32 |
| 130 | 2.9–3.0 | 32 |
| 131 | 2.9–3.0 | 32 |
| 132 | 2.9–3.0 | 32 |

*The ozone concentration is changed manually after indicated cycle. Every third cycle (1, 4, 7 etc.) and the data points from the electrochemical cleaning are excluded from the data analysis.

Figure 15:
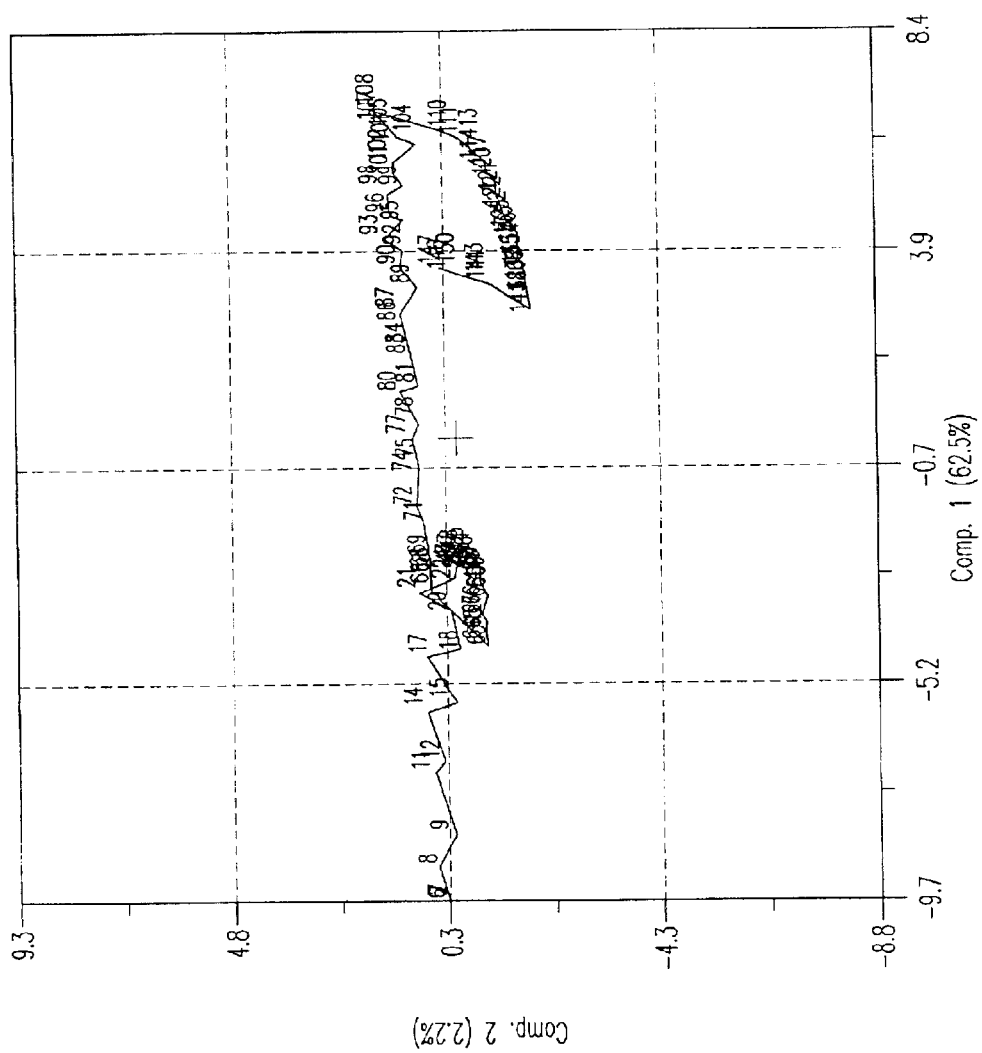

Record for Measurement with the Electric Tongue 000927 (FIG. 15)

New milli-q water (just before warming up and before start), packing ring nr 1 and a warm ozone generator are used for experiment 5. Conductivity measurements are performed as well.

| Cycle | Conc $O_3$ (ppm) | Temp ° C. |
|---|---|---|
| 1 | 0 | 31 |
| 2 | 0 | 31 |
| 3 | 0 | 31 |
| Cond | 1.6 µS | |
| 4 | 0 | 31 |
| 5 | 0 | 31 |
| 6* | 0 | 31 |
| 7 | 0.3–1.7 | 31 |
| 8 | 1.7–2.3 | 31 |
| 9 | 2.3–2.6 | 31 |
| 10 | 2.7–2.8 | 31 |
| 11 | 2.8–2.9 | 31 |
| 12 | 2.9 | 31 |
| Cond | 4.5 µS | |
| 13 | 2.9–3.0 | 31 |
| 14 | 2.9–3.0 | 31 |
| 15 | 2.9–3.0 | 31 |
| 16 | 2.9–3.0 | 31 |
| 17 | 2.9–3.0 | 31 |
| 18 | 2.9–3.0 | 31 |
| Cond | 7.3 µS | |
| 19 | 2.9–3.0 | 31 |
| 20 | 2.9–3.0 | 31 |
| 21* | 2.9–3.0 | 31 |
| 22 | 2.4–1.7 | 31 |
| 23 | 1.7–1.4 | 31 |
| 24 | 1.4–1.1 | 31 |
| 25 | 1.0–0.9 | 31 |
| 26 | 0.9–0.8 | 31 |
| 27 | 0.8 | 31 |
| Cond | 9.1 µS | |
| 28 | 0.7–0.6 | 31 |
| 29 | 0.7–0.6 | 31 |
| 30 | 0.6 | 31 |
| 31 | 0.6 | 31 |
| 32 | 0.6–0.5 | 31 |
| 33 | 0.5 | 31 |
| 34 | 0.5 | 31 |
| 35 | 0.5–0.4 | 31 |
| 36 | 0.4 | 31 |
| 37 | 0.4 | 31 |
| 38 | 0.4 | 31 |
| 39 | 0.4–0.3 | 31 |
| 40 | 0.3 | 32 |
| 41 | 0.3 | 32 |
| 42 | 0.3 | 32 |
| 43 | 0.2 | 32 |
| 44 | 0.2 | 32 |
| 45 | 0.2 | 32 |
| 46 | 0.2 | 32 |
| 47 | 0.1 | 32 |
| 48 | 0.1 | 32 |
| 49 | 0.1 | 32 |
| 50 | | |
| 51 | 0 | 32 |
| 52 | | |
| 53 | | |
| 54 | | |
| 55 | | |
| 56 | | |
| 57 | | |
| 58 | | |
| 59 | 0 | 32 |
| 60 | | |
| Cond | 7.6 µS | |
| 61 | 0 | 32 |
| 62 | | |
| 63* | | |
| 64 | | |
| 65 | 2.3–2.8 | 32 |
| 66 | 2.8–2.9 | |
| 67 | | |
| 68 | | |
| 69 | | |
| 70 | | |
| 71 | | |
| 72 | | |
| 73 | | |

-continued

| Cycle | Conc O$_3$ (ppm) | Temp °C. |
|---|---|---|
| 74 | | |
| 75 | | |
| 76 | | |
| 77 | | |
| 78 | | |
| 79 | | |
| 80 | | |
| 81 | | |
| 82 | | |
| 83 | | |
| 84 | | |
| 85 | | |
| 86 | | |
| 87 | | |
| 88 | | |
| 89 | | |
| 90 | | |
| 91 | | |
| 92 | | |
| 93 | | |
| 94 | | |
| 95 | | |
| 96 | | |
| 97 | | |
| 98 | | |
| 99 | | |
| 100 | | |
| 101 | | |
| 102 | | |
| 103 | | |
| 104 | | |
| 105 | | |
| 106 | | |
| 107 | | |
| 108* | | 33 |
| 109 | | 33 |
| 110 | 1.9–1.4 | 32 |
| 111 | 1.4–1.2 | 32 |
| Cond | 18.4 µS | |
| 112 | 1.0–0.9 | 32 |
| 113 | 0.9–0.8 | 32 |
| 114 | 0.8–0.7 | 32 |
| 115 | 0.7 | 32 |
| 116 | 0.7 | 32 |
| 117 | 0.7 | 32 |
| 118 | 0.6 | 32 |
| 119 | 0.6 | 32 |
| 120* | 0.6 | 32 |
| 121 | 0.5 | 32 |
| 122 | 0.5 | 32 |
| 123 | 0.5 | 32 |
| 124 | 0.4 | 31 |
| 125 | 0.4 | 31 |
| 126 | 0.4 | 31 |
| 127 | 0.3 | 31 |
| 128 | 0.3 | 31 |
| 129 | 0.3 | 31 |
| 130 | 0.3–0.2 | 31 |
| 131 | 0.2 | |
| 132 | 0.2 | |
| 133 | 0.2 | 32 |
| 134 | 0.2–0.1 | 32 |
| 135 | 0.2–0.1 | 32 |
| 136 | 16.9 µS | |
| 137 | 0.1 | 32 |
| 138 | 0.1 | 32 |
| 139 | 0.1 | 32 |
| 140 | 0.1 | 32 |
| 141* | 0.1 | 32 |
| 142 | 0.6–0.9 | 32 |
| 143 | 0.9–1.0 | 32 |
| 144* | 1.0 | 32 |
| Cond | 15.6 µS | |
| 145 | 2.3–2.8 | 31 |
| 146 | 2.8–2.9 | 31 |
| 147 | 2.9–3.0 | 31 |
| 148 | | 31 |
| 149 | | 31 |
| 150 | 1.8–1.6 | 31 |

*The ozone concentration is changed manually after indicated cycle.
Cond = conductivity
Every third cycle (1, 4, 7 etc.) and the data points from the electrochemical cleaning are excluded from the data analysis.

Figure 16:
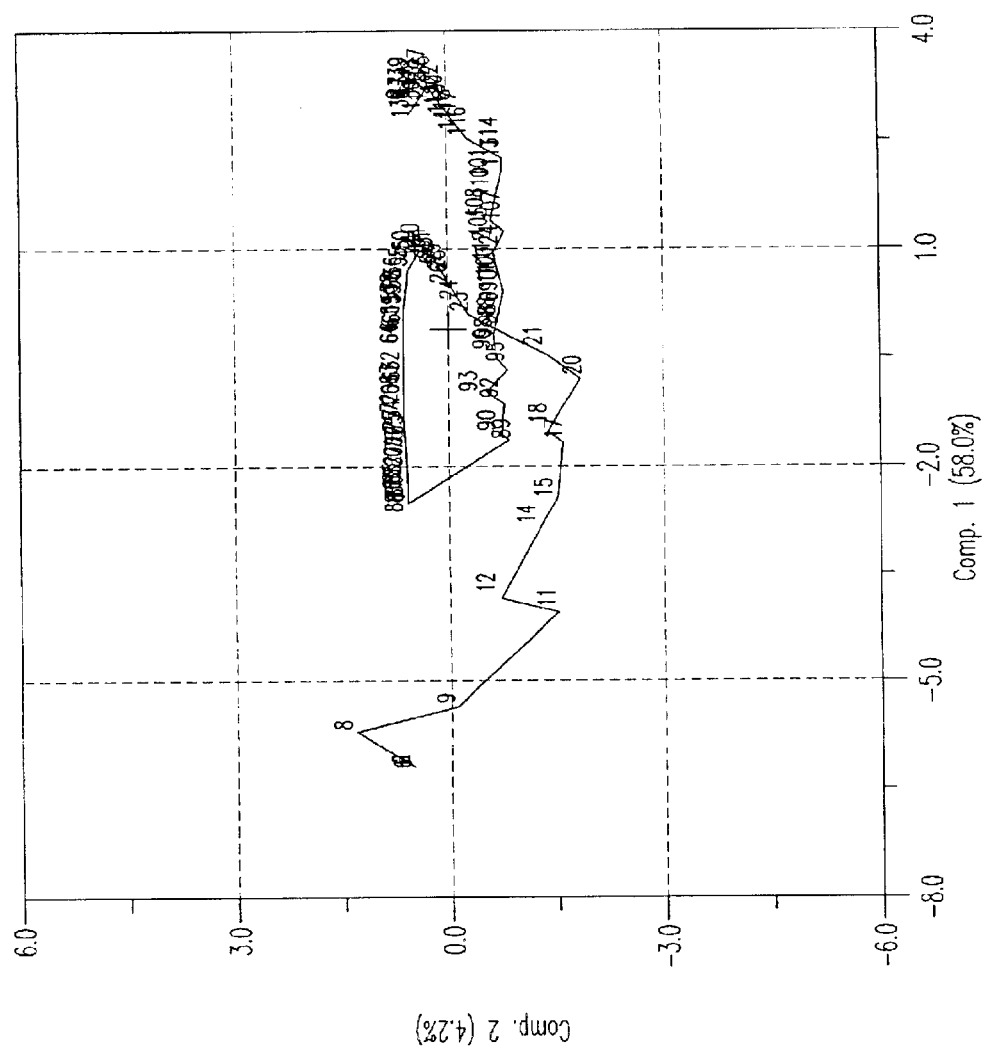

Record for Measurement with the Electric Tongue 001002 (FIG. 16)

New milli-q water (just before warming up and before start), packing ring nr 2 and a warm ozone generator are used for experiment 6. Conductivity measurements are performed as well.

| Cycle | Conc O$_3$ (ppm) | Temp °C. |
|---|---|---|
| 1 | 0 | 32 |
| 2 | 0 | 32 |
| 3 | 0 | 32 |
| Cond | 2.4 µS | |
| 4 | 0 | 32 |
| 5 | 0 | 32 |
| 6* | 0 | 32 |
| 7 | 0.3–1.2 | 32 |
| 8 | 1.2–2.3 | 32 |
| 9 | 2.3–2.7 | 32 |
| 10 | 2.8–2.9 | 32 |
| 11 | 2.9 | 32 |
| 12 | 2.9–3.0 | 32 |
| Cond | 3.9 µS | |
| 13 | 2.9–3.0 | 32 |
| 14 | 2.9–3.0 | 32 |
| 15 | 2.9–3.0 | 32 |
| 16 | 2.9–3.0 | 32 |
| 17 | 2.9–3.0 | 32 |
| 18 | 2.9–3.0 | 32 |
| 19 | 5.8 µS | 32 |
| 20 | 2.9–3.0 | 32 |
| 21* | 2.9–3.0 | 32 |
| 22 | | 32 |
| 23 | 1.8–1.5 | 32 |
| 24 | 1.5–1.3 | 32 |
| 25 | 1.2–1.1 | 32 |
| 26 | 1.0–1.1 | 32 |
| 27 | 1.0 | 32 |
| Cond | 7.9 µS | |
| 28 | 0.9 | 32 |
| 29 | 0.9 | 32 |
| 30 | 0.8 | 32 |
| 31 | 0.8–0.7 | 32 |
| 32 | 0.7 | 32 |
| 33 | 0.7 | 32 |
| 34 | 0.6 | 32 |
| 35 | 0.6 | 32 |
| 36 | 0.6 | 32 |
| 37 | 0.6–0.5 | 32 |
| 38 | 0.5 | 32 |
| 39 | 0.5 | 32 |
| 40 | 0.5–0.4 | 32 |
| 41 | 0.4 | 32 |
| 42 | 0.4 | 32 |
| 43 | 0.4 | 32 |
| 44 | 0.4–0.3 | 32 |
| 45 | 0.4–0.3 | 32 |
| 46 | 0.3 | 32 |
| 47 | 0.3 | 32 |
| 48 | 0.2–0.3 | 32 |
| 49 | 0.2 | 32 |
| 50 | 0.2 | 32 |

-continued

| Cycle | Conc O₃ (ppm) | Temp ° C. |
|---|---|---|
| 51 | 0.2–0.1 | 32 |
| Cond | 7.9 µS | |
| 52 | 0.1 | 32 |
| 53 | 0.1 | 32 |
| 54 | | |
| 55 | | |
| 56 | | |
| 57 | | |
| 58 | | |
| 59 | | |
| 60 | | |
| 61 | | |
| 62 | | |
| 63* | | |
| 64 | | |
| 65 | | |
| 66 | | |
| 67 | | |
| 68 | | |
| 69 | | |
| 70 | | |
| 71 | | |
| 72 | | |
| 73 | | |
| 74 | | |
| 75 | | |
| 76 | | |
| 77 | | |
| 78 | | |
| 79 | | |
| 80 | | |
| 81 | | |
| 82 | | |
| 83 | | |
| 84 | | |
| 85 | | |
| 86 | | |
| 87* | | |
| Cond | 5.1 µS | |
| 88 | 1.2–2.6 | 26 |
| 89 | 2.6–3.0 | 26 |
| 90 | 2.9–3.0 | 26 |
| 91 | 2.9–3.0 | 26 |
| 92 | 2.9–3.0 | 26 |
| 93 | | 26 |
| 94 | | |
| 95 | | |
| 96 | | |
| 97 | | |
| 98 | 2.9–3.0 | 26 |
| 99 | | |
| 100 | | |
| 101 | | |
| 102 | 2.9–3.0 | 26 |
| Cond | 8.2 µS | |
| 103 | | |
| 104 | | |
| 105 | | 26 |
| 106 | | |
| 107 | 2.9–3.0 | 26 |
| 108 | | |
| 109 | 2.9–3.0 | 26 |
| 110 | | 26 |
| Cond | 9.4 µS | |
| 111 | 2.9–3.0 | 26 |
| 112 | 2.9–3.0 | 26 |
| 113 | | |
| 114* | 2.9–3.0 | 26 |
| 115 | | 26 |
| 116 | | 26 |
| 117 | | 26 |
| 118 | | 26 |
| 119 | 1.7–1.6 | 26 |
| 120 | 1.6–1.5 | 26 |
| 121 | | 26 |
| 122 | | 26 |
| 123 | | 26 |
| 124 | | 26 |
| 125 | | |
| 126 | 1.2 | 26 |
| 127 | | |
| 128 | | |
| 129 | 1.0 | |
| 130 | | |
| 131 | 0.9 | 26 |
| 132 | | |
| 133 | | |
| 134 | 0.8 | |
| 135 | | |
| 136 | 0.7 | 25 |
| 137 | | |
| 138 | 0.7 | 25 |
| 139 | | |
| 140 | | |
| 141 | 0.6 | 25 |
| 142 | | |
| 143 | 0.5 | 25 |
| 144 | | |
| 145 | 0.4 | 25 |
| 146 | 0.4 | 25 |

*The ozone concentration is changed manually after indicated cycle.
Cond = conductivity
Every third cycle (1, 4, 7 etc.) and the data points from the electrochemical cleaning are excluded from the data analysis.

Figure 17:
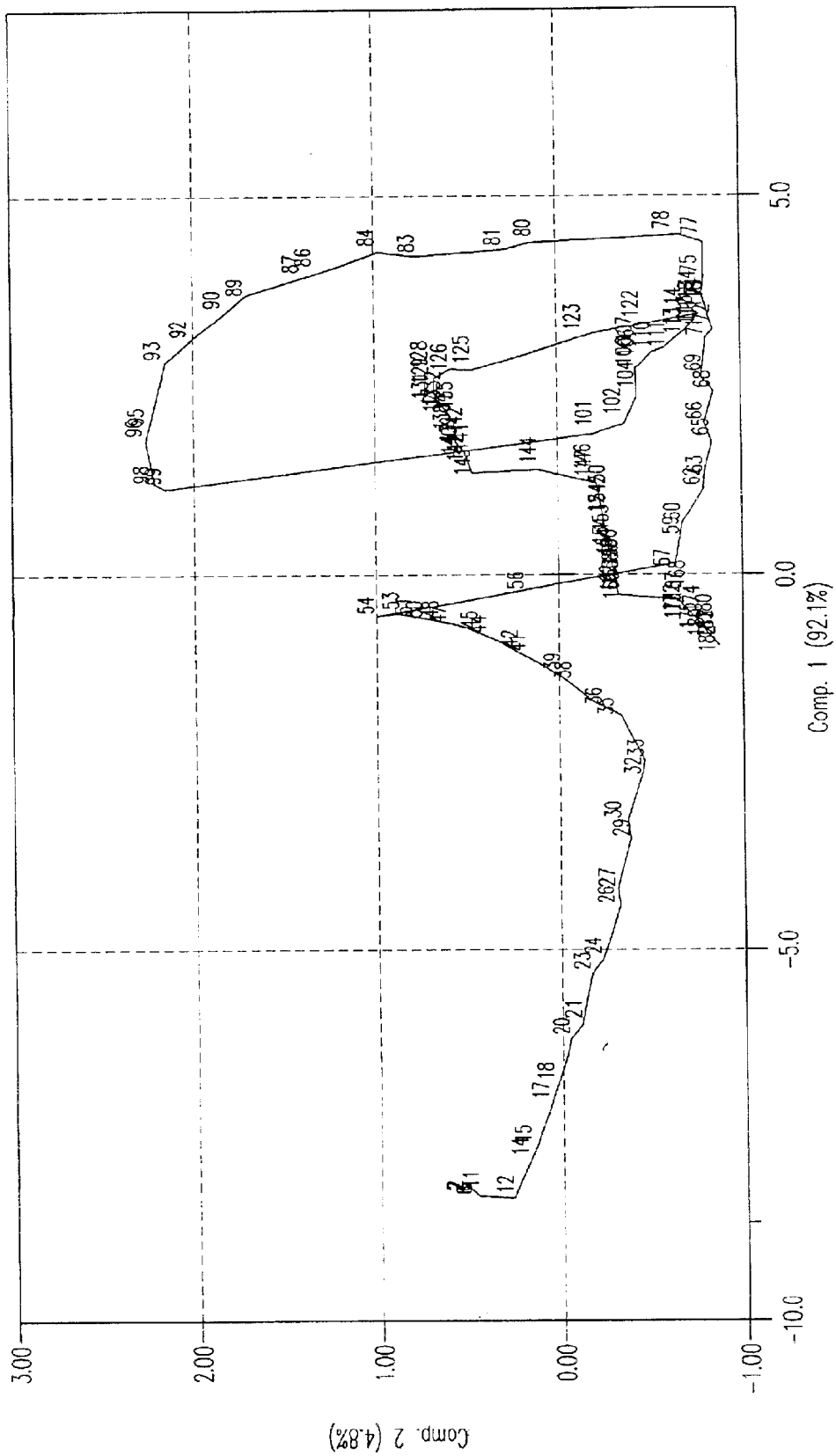

Record for Measurement with the Electric Tongue 001013 (FIG. 17)

New milli-q water (just before start), packing ring nr 2 and a cold ozone generator are used for experiment 7.

| Cycle | Conc O₃ (ppm) | Temp ° C. |
|---|---|---|
| 2 | 0.04 | 22.6 |
| 3 | 0.04 | 22.6 |
| 5 | 0.04 | 22.6 |
| 6 | 0.04 | 22.6 |
| 8 | 0.04 | 22.6 |
| 9 | 0.05 | 22.6 |
| 11 | 0.04 | 23.6 |
| 14 | 2.90 | 23.6 |
| 17 | 2.99 | 23.6 |
| 18 | 3.01 | 23.6 |
| 23 | 3.00 | 24.6 |
| 24 | 2.94 | 24.6 |
| 26 | 2.99 | 24.6 |
| 27 | 3.03 | 24.6 |
| 32 | 2.98 | 25.7 |
| 33 | 2.97 | 25.7 |
| 47 | 0.73 | 26.7 |
| 48 | 0.67 | 26.7 |
| 50 | 0.52 | 26.7 |
| 51 | 0.47 | 26.7 |
| 53 | 0.34 | 26.7 |
| 54 | 0.29 | 26.7 |
| 59 | 2.99 | 30.8 |
| 60 | 3.00 | 30.8 |
| 62 | 2.96 | 30.8 |
| 63 | 2.97 | 30.8 |
| 66 | 2.97 | 31.8 |
| 68 | 2.97 | 31.8 |
| 69 | 2.91 | 31.8 |
| 71 | 2.97 | 31.8 |
| 72 | 2.93 | 31.8 |
| 75 | 2.98 | 31.8 |
| 77 | 2.97 | 31.8 |
| 89 | 0.35 | 32.8 |

-continued

| Cycle | Conc O₃ (ppm) | Temp ° C. |
|---|---|---|
| 90 | 0.29 | 32.8 |
| 92 | 0.13 | 32.8 |
| 93 | 0.10 | 32.8 |
| 95 | 0.03 | 32.8 |
| 96 | 0.03 | 32.8 |
| 98 | 0.03 | 32.8 |
| 99 | 0.03 | 32.8 |
| 104 | 3.01 | 32.8 |
| 105 | 3.01 | 32.8 |
| 107 | 2.97 | 32.8 |
| 108 | 2.98 | 32.8 |
| 110 | 3.00 | 32.8 |
| 111 | 2.98 | 32.8 |
| 113 | 2.99 | 32.8 |
| 114 | 2.99 | 32.8 |
| 116 | 2.96 | 32.8 |
| 117 | 2.96 | 32.8 |
| 119 | 2.95 | 32.8 |
| 120 | 2.96 | 32.8 |
| 128 | 1.00 | 32.8 |
| 129 | 0.97 | 32.8 |
| 131 | 0.96 | 32.8 |
| 132 | 0.97 | 32.8 |
| 134 | 0.98 | 32.8 |
| 135 | 1.02 | 32.8 |
| 137 | 1.00 | 32.8 |
| 138 | 0.99 | 32.8 |
| 140 | 0.97 | 32.8 |
| 141 | 0.98 | 32.8 |
| 143 | 0.98 | 32.8 |
| 146 | 1.97 | 32.8 |
| 147 | 1.97 | 32.8 |
| 149 | 2.02 | 32.8 |
| 150 | 2.02 | 32.8 |
| 152 | 1.99 | 32.8 |
| 155 | 2.00 | 32.8 |
| 156 | 2.02 | 32.8 |
| 158 | 1.97 | 32.8 |
| 159 | 1.97 | 32.8 |
| 161 | 1.98 | 32.8 |
| 162 | 2.00 | 32.8 |
| 164 | 1.97 | 32.8 |
| 165 | 2.00 | 32.8 |
| 168 | 3.02 | 32.8 |
| 170 | 2.99 | 32.8 |
| 171 | 2.99 | 32.8 |
| 174 | 2.96 | 32.8 |
| 176 | 3.01 | 32.8 |
| 177 | 2.98 | 32.8 |
| 179 | 3.02 | 32.8 |
| 183 | 3.02 | 33.6 |
| 185 | 2.98 | 33.9 |
| 186 | 2.97 | 33.9 |

The ozone concentration is changed automatically, see the table below. Every third cycle (1, 4, 7 etc.) (not included in the table above), the cycles with an ozone concentration that differs more than 0,1 ppm (not included in the table above) and data points from the electrochemical cleaning are excluded from the data analysis.

Automatic program for the ozone generator:

| Conc O₃ (ppm) | Time (min) |
|---|---|
| 0 | 30 |
| 3 | 60 |
| 0 | 60 |
| 3 | 60 |
| 0 | 60 |
| 3 | 60 |
| 1 | 60 |
| 2 | 60 |
| 3 | 60 |

Figure 18:
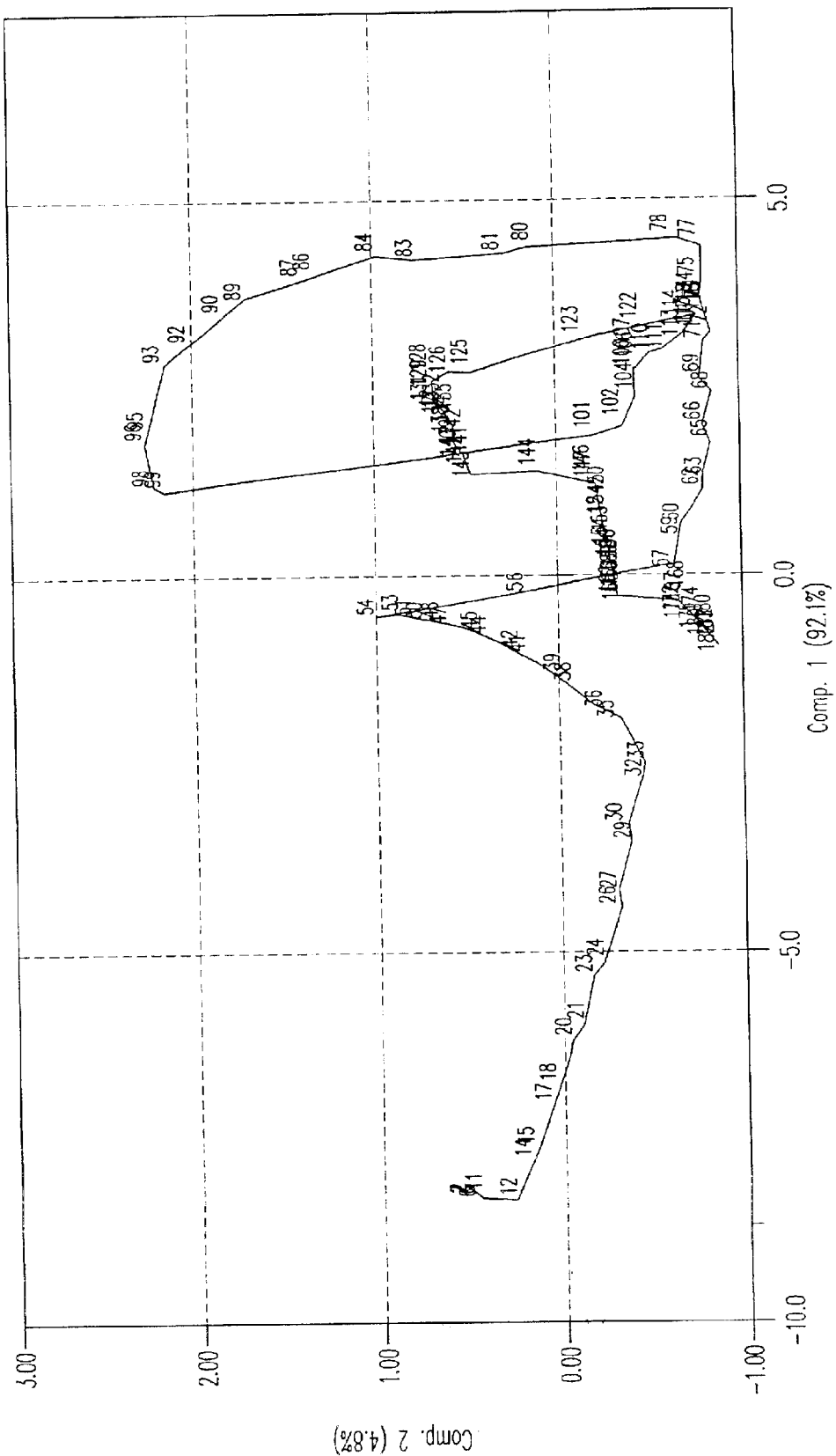

Record for Measurement with the Electric Tongue 001014 (FIG. 18)

New milli-q water (just before start), packing ring nr 2 and a cold ozone generator are used for experiment 8.

| Cycle | Conc O₃ (ppm) | Temp ° C. |
|---|---|---|
| 3 | 0.02 | 21.3 |
| 5 | 0.03 | 20.5 |
| 6 | 0.05 | 21.5 |
| 8 | 0.05 | 21.5 |
| 9 | 0.05 | 21.5 |
| 11 | 0.06 | 21.5 |
| 12 | 0.07 | 21.5 |
| 42 | 1.47 | 25.7 |
| 45 | 1.21 | 25.7 |
| 47 | 1.08 | 25.7 |
| 48 | 0.99 | 25.7 |
| 50 | 0.90 | 25.7 |
| 51 | 0.81 | 25.7 |
| 53 | 0.72 | 25.7 |
| 54 | 0.64 | 25.7 |
| 56 | 0.56 | 26.2 |
| 57 | 0.48 | 26.7 |
| 62 | 2.99 | 26.7 |
| 63 | 2.90 | 26.7 |
| 66 | 2.90 | 26.7 |
| 69 | 2.95 | 30.8 |
| 71 | 2.98 | 30.8 |
| 72 | 2.96 | 30.8 |
| 74 | 2.92 | 30.8 |
| 77 | 2.98 | 31.8 |
| 78 | 3.02 | 31.8 |
| 80 | 3.00 | 31.8 |
| 92 | 0.70 | 31.8 |
| 96 | 0.41 | 31.8 |
| 98 | 0.32 | 31.8 |
| 99 | 0.25 | 31.8 |
| 101 | 0.19 | 31.8 |
| 111 | 3.00 | 32.8 |
| 113 | 2.98 | 32.8 |
| 114 | 3.00 | 32.8 |
| 116 | 2.95 | 32.8 |
| 117 | 2.98 | 32.8 |
| 119 | 2.96 | 32.8 |
| 120 | 3.00 | 32.8 |
| 122 | 2.95 | 32.8 |
| 123 | 2.96 | 32.8 |
| 135 | 0.98 | 32.8 |
| 137 | 1.01 | 32.8 |
| 140 | 0.99 | 32.8 |
| 143 | 0.98 | 32.8 |
| 144 | 1.00 | 32.8 |
| 149 | 1.99 | 32.8 |
| 150 | 1.99 | 32.8 |
| 152 | 2.00 | 32.8 |
| 153 | 2.02 | 32.8 |
| 155 | 2.01 | 32.8 |
| 158 | 1.97 | 32.8 |
| 159 | 1.98 | 32.8 |
| 161 | 2.00 | 32.8 |
| 162 | 2.01 | 32.8 |
| 164 | 1.99 | 32.8 |
| 165 | 2.00 | 32.8 |
| 167 | 2.00 | 32.8 |
| 168 | 1.99 | 32.8 |
| 173 | 3.03 | 32.8 |

-continued

| Cycle | Conc O$_3$ (ppm) | Temp °C. |
|---|---|---|
| 176 | 3.00 | 32.8 |
| 179 | 2.95 | 32.8 |
| 180 | 2.97 | 32.8 |
| 182 | 2.97 | 32.8 |
| 183 | 2.98 | 32.8 |
| 185 | 3.03 | 32.8 |
| 188 | 2.96 | 32.8 |

The ozone concentration is changed automatically.
Every third cycle (1, 4, 7 etc.) (not included in the table above), the cycles with an ozone concentration that differs more than 0,1 ppm (not included in the table above) and data points from the electrochemical cleaning are excluded from the data analysis.

What is claimed is:

1. An ozone detection system based on voltammetry, for detecting the presence and/or concentration of ozone in a liquid sample, comprising
    at least one working electrode comprised of one or more of the metals selected from the group consisting of Rh, Pt, Au, Os, Ru, Ni, Ti, and Re;
    a counter electrode;
    a programmable pulse generator capable of applying a predetermined sequence of energizing pulses to said at least one working electrode;
    a recording device for recording the output from said at least one working electrode generated in response to the applied pulse sequence;
    a sampling device for sampling values of said output at predetermined intervals;
    a memory for storing the sampled values in a matrix;
    a processing unit (PC) for performing a multivariate analysis of said matrix, and predicting a concentration of ozone based on the results of said multivariate analysis; and
    a display device for displaying the result of said multivariate analysis.

2. The ozone detection system as claimed in claim 1, wherein said at least one working electrode is made of Rh.

3. The ozone detection system as claimed in claim 1, wherein said at least one working electrode and said counter electrode are provided on-line in a processing plant.

4. The ozone detection system as claimed in claim 1, wherein the at least one working electrode comprises two or more working electrodes.

5. The ozone detection system as claimed in claim 1, wherein the number of working electrodes is four to six.

6. The ozone detection system as claimed in claim 1, wherein the at least one working electrode comprises a plurality of working electrodes made of different materials.

7. The ozone detection system as claimed in claim 1, further comprising a rod shaped support member wherein electrodes are imbedded, such that a surface portion of the each electrode is exposed.

8. The ozone detection system as claimed in claim 7, further comprising an auxiliary electrode provided as a ring electrode on the periphery of said rod shaped support member.

9. The ozone detection system as claimed in claim 1, further comprising an essentially planar plate member of an inert material on which a plurality of the at least one working electrode are provided as strips of metal.

10. The ozone detection system as claimed in claim 9, wherein the inert material comprises ceramic.

11. The ozone detection system as claimed in claim 1, wherein said at least one working electrode and said counter electrode are provide inside a tube segment forming part of a circulation system of a processing plant in which it is desired to monitor the presence or concentration of ozone, and wherein said at least one working electrode and said counter electrode have electrical through-connections through said tube segment at least at one end of each of said at least one working electrode and said counter electrode, for connection to external equipment.

12. The ozone detection system as claimed in claim 1, further comprising auxiliary electrodes for measuring conductivity.

* * * * *